United States Patent [19]

Marx et al.

[11] 4,011,315
[45] Mar. 8, 1977

[54] 21-ACETALS AND MIXED ACETALS OF STEROIDAL 21-ALDEHYDES, INTERMEDIATES AND METHODS OF PREPARATION

[75] Inventors: Michael Marx, Sunnyvale; Denis John Kertesz, Menlo Park, both of Calif.

[73] Assignee: Syntex (U.S.A.) Inc., Palo Alto, Calif.

[22] Filed: July 7, 1975

[21] Appl. No.: 593,903

[52] U.S. Cl. .................. 424/241; 260/239.55 D; 260/397.45; 260/349

[51] Int. Cl.² ............................................. C07J 5/00

[58] Field of Search ............. 260/239.55 D, 397.45

[56] References Cited

UNITED STATES PATENTS 3,519,659 7/1970 Schmidlin et al. ............ 260/397.45
3,519,660 7/1970 Schmidlin et al. ............ 260/397.45

*Primary Examiner*—Elbert L. Roberts
*Attorney, Agent, or Firm*—Alan M. Krubiner; William B. Walker; Natalie Jensen

[57] ABSTRACT

21-acetals and mixed acetals of steroids of the corticoid series are prepared from the corresponding 21-hydroxy steroids and have utility as anti-inflammatory agents.

29 Claims, No Drawings

21-ACETALS AND MIXED ACETALS OF STEROIDAL 21-ALDEHYDES, INTERMEDIATES AND METHODS OF PREPARATION

SUMMARY

The present invention relates to cyclopentanophenanthrene derivatives and to certain novel compounds obtained as intermediates.

More particularly, the present invention relates to compounds represented by the formula:

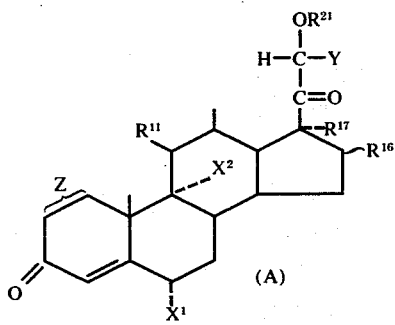

(A)

wherein $R^{11}$ is chloro or hydroxy; $R^{16}$ independently is methyl; $R^{17}$ independently is hydroxy or acyloxy having 2 to 8 carbon atoms or $R^{16}$ and $R^{17}$ taken together are 16α,17α-isopropylidenedioxy; $R^{21}$ is lower alkyl having 1 to 8 carbon atoms; $X^1$ and $X^2$ are independently hydrogen, chloro or fluoro, with the proviso that when $R^{11}$ is chloro, $X^2$ is chloro; Y is $OR^{21}$, $SR^{21'}$, bromo, chloro, cyano, thiocyano or azido in which $R^{21'}$ is lower alkyl having 1 to 8 carbon atoms or phenyl and $R^{21}$ is defined as above, but independent thereof, and Z is a single or double bond.

A preferred subclass of compounds within the class defined by formula (A) are those compounds wherein Y is $OR^{21}$. Preferred compounds within this subclass are the symmetrical 21,21-bis-alkyl esters. Particularly preferred compounds are the 21,21-bis-methyl ethers.

In addition, the present invention relates to certain compounds obtained as intermediates in the preparation of compounds of Formula (A) and exhibiting similar pharmacological activity. These novel intermediates are represented by the formulas:

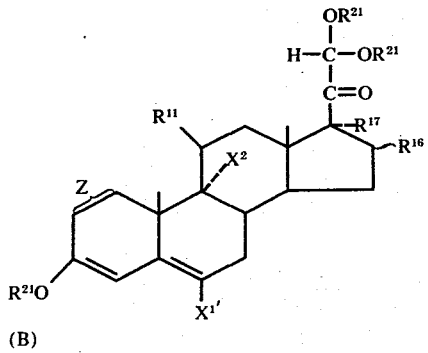

(B)

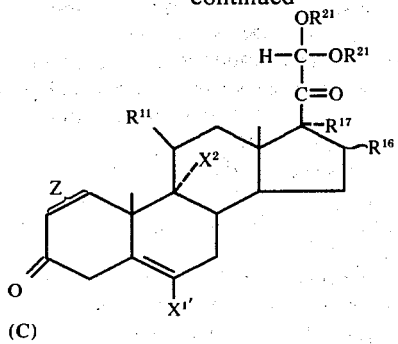

(C)

wherein $X^{1'}$ is hydrogen, chloro and fluoro when Z is a single bond and chloro or fluoro when Z is a double bond; $R^{11}$, $R^{16}$, $R^{17}$, $R^{21}$ and $X^2$ are as previously defined and all $R^{21}$s are identical.

Preferred compounds embraced by Formulas (B) and (C) are those wherein $R^{21}$ is methyl or ethyl.

The compounds of the instant invention are potent topical anti-inflammatory agents. Although the instant compounds exhibit low systemic activity in the rat as measured in standard assays, e.g. Rat Thymolytic Assay and the Anti-inflammatory Assay Utilizing Carrageenan-induced Rat Paw Edema, they exhibit high topical activity in humans as measured in the Stoughton-McKenzie Assay (Human Vasoconstrictor Assay). In spite of the fact that systemic effects such as adrenal atrophy, mineralocorticoid effects and collagen disorders may be produced by large doses of the instant compounds if administered for long periods of time, the favorable topical/systemic activity ratio of the instant compounds permits the use of such small doses that these systemic effects are minimized. This combination of high topical anti-inflammatory activity coupled with negligible systemic activity renders the instant compounds highly suitable for the alleviation of inflammatory disorders.

The present invention further relates to a method for treating symptoms associated with inflammatory disorders, which method comprises administering an effective amount of a compound selected from those represented by formulas (A), (B), and (C), or a pharmaceutical composition incorporating such a compound as an active ingredient.

The present invention still further relates to pharmaceutical compositions useful for treating inflammatory disorders. These compositions comprise an effective amount of a compound selected from those represented by formulas (A), (B), and (C) in admixture with a pharmaceutically acceptable non-toxic carrier.

Suitable carriers or medicament vehicles for topical application of the novel steroids of the instant invention include creams, ointments, lotions, emulsions, solutions, and the like. For example, a suitable ointment for topical application of compounds of the instant invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and the mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding mono-ester of other fatty acids such as oleic acid and palmitic acid; and 0 to 20 wt. percent of the penetrant such as dimethyl sulfoxide, dimethylacetamide, dimethylformamide, and the like.

The concentration of cortical steroid in pharmaceutical compositions suitable for topical application will vary depending upon the particular activity of the steroid used in conjunction with the condition and subject to be treated. In general, topical preparations containing 0.005 to 1% by weight of the active steroid are advantageously employed.

In the specification and claims the following definitions apply:

The wavy line (∼) used in the depicted formulas indicates that the substituent attached to those positions can be in either the ($\alpha$) or ($\beta$) configuration.

The broken line ( - - - ) used in the depicted formulas indicates that the substituent attached to those positions is in the $\alpha$ configuration.

The unbroken line (—) used in the depicted formulas indicates that the substituent attached to those positions is in the $\beta$ configuration.

The term "lower alkyl" defines aliphatic hydrocarbons containing from 1 to 8 carbon atoms including all isomers thereof. Typical lower alkyl groups are methyl, ethyl, n-propyl, isopropyl, n-butyl, sec-butyl, n-amyl, n-hexyl, n-heptyl, n-octyl, and so forth.

The term "acyloxy" refers to those esters employed in the cortical steroid art having from 2 to 8 carbon atoms and being derived from alkanoic or phenyl carboxylic acids. Typical acyloxy groups expressed as the ester include for example acetate, propionate, butyrate, valerate, caproate, enanthate, carpyrlate, benzoate and the like.

Compounds of Formula (A) wherein Y and $OR^{21}$ are not identical exist in two epimeric forms, i.e., the 21(R) and 21(S) forms. Accordingly, all nomenclature, formulas and discussion herein is intended to refer to both forms and mixtures thereof unless otherwise specified.

DETAILED DESCRIPTION

The present invention, in a further aspect, is directed to methods for the preparation of compounds of Formulas (A), (B), and (C) according to the following reaction sequences:

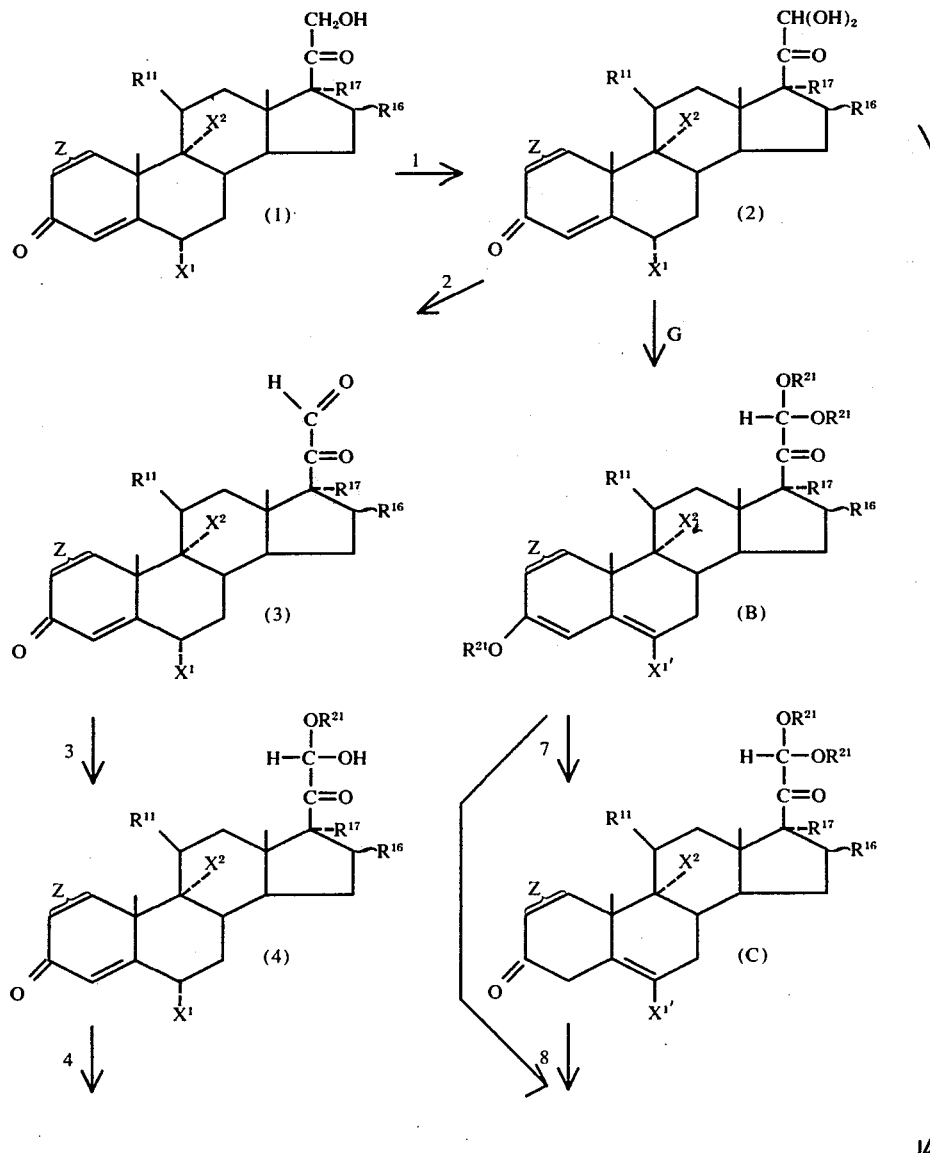

-continued

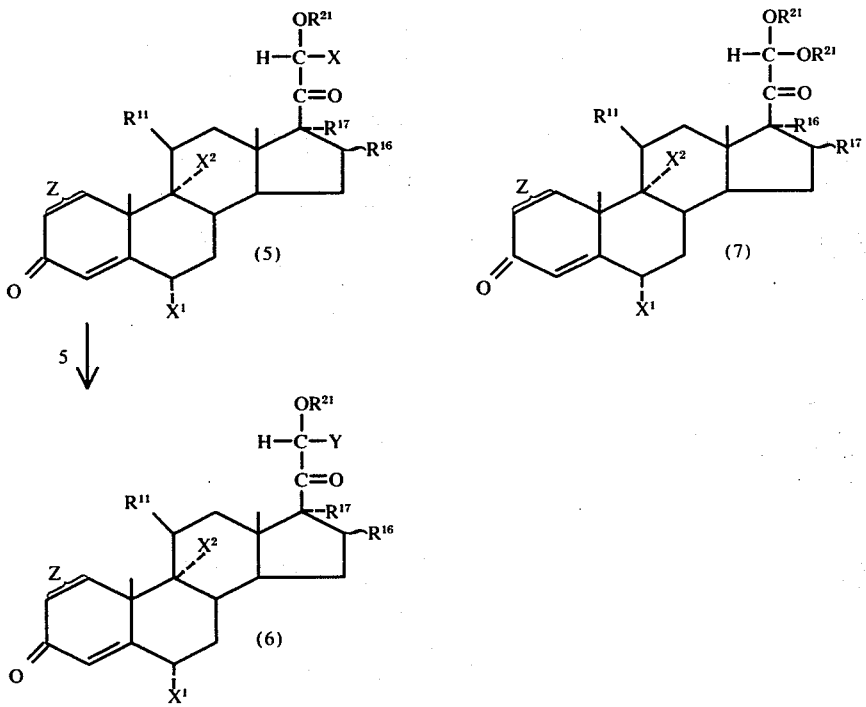

In the above formulas $R^{11}$, $R^{16}$, $R^{17}$, $R^{21}$, $X^1$, $X^2$, and Z are as previously defined; Y is $OR^{21}$, $SR^{21'}$ cyano, thiocyano or azido in which $R^{21}$ and $R^{21'}$ are as previously defined; X is chloro or bromo; and $X^{1'}$ is hydrogen, chloro or fluoro when Z is a single bond and chloro and fluoro when Z is a double bond.

With reference to reaction steps 1–5, a 21-hydroxy steroid (1) is contacted with air in the presence of a copper (II) catalyst such as cupric acetate to yield the 21-aldehyde hydrate (2). The reaction is preferably conducted in methanol at a temperature of 50° to 30° C. for a period of 30 minutes to 6 hours.

The 21-aldehyde hydrate (2) is then heated under vacuum at a temperature of 100° C. for a period of 30 minutes to 3 hours to yield the 21-aldehyde (3) which is reacted with a lower alkanol containing 1 to 8 carbon atoms at a temperature of 20° to 60° C. for a period of 15 minutes to 1 hour to yield the 21-aldehyde hemiacetal (4).

Reaction of the 21-aldehyde hemiacetal (4) with a suitable halogenating agent such as methane sulfonyl chloride, thionyl chloride, or thionyl bromide in the presence of an organic base such as triethylamine, pyridine and the like yields the 21-halo-21-alkyl ether (5). The reaction is preferably conducted in a chlorinated organic solvent such as methylene chloride, chloroform, 1,1-dichloroethane and the like for a period of 1 to 16 hours and a temperature of −20° to +10° C.

The thus obtained 21-halo-21-alkyl ether (5) is then used to prepare the 21-aldehyde acetal ((6), Y=$OR^{21}$), the 21-azido-21-alkyl ether ((6), Y=azido), the 21-thiocyano-21-alkyl ether ((6), Y=thiocyano), the 21-cyano-21-alkyl ether ((6), Y=cyano), the 21-thiophenyl-21-alkyl ether ((6), Y=thiophenyl), and the 21-thioalkyl-21-alkyl ether ((6), Y=thioalkyl).

Preparation of the 21-aldehyde acetal ((6), Y=$OR^{21}$) is accomplished by treating the 21-halo-21-alkyl ether (5) with an alkali metal alkoxide, preferably a sodium alkoxide such as sodium methoxide, sodium ethoxide, etc. The reaction is conducted in a solvent medium usually containing the alkanol corresponding to the alkoxide utilized although a solvent inert to the other reactants may be employed. Reaction temperatures are peferably maintained at 20° to 60° C. for a period of 2 to 6 hours.

The 21-azido-21-alkyl ether ((6), Y=azido) is prepared by treating the 21-halo-21-alkyl ether (5) with an alkali metal azide, preferably sodium azide, in an aprotic inert organic solvent such as dimethylformamide, acetone, hexamethylphosphoramide, dimethyl sulfoxide and the like. The reaction is preferably conducted at a temperature of 20° to 60° C. for a period of 2 to 12 hours.

Preparation of the 21-thiocyano-21-alkyl ether ((6), Y=thiocyano), the 21-cyano-21-alkyl ether ((6), Y=cyano), the 21-thiophenyl-21-alkyl ether, ((6), Y=thiophenyl) and the 21thioalkyl-21-alkyl ether ((6), Y=thioalkyl) is accomplished according to the procedure outlined in the previous paragraph, i.e., the 21-halo-21-alkyl ether (5) is treated with a suitable alkali metal salt such as potassium thiocyanate, sodium cyanide, sodium thiophenylate or a sodium thioalkylate in an aprotic inert organic solvent such as dimethylformamide, acetone, hexamethylphosphoramide, dimethyl sulfoxide and the like at a temperature of 20 to 80° C. for a period of 2 to 16 hours.

Compounds of Formula (A) having identical $R^{21}$ groups are conveniently prepared via reaction steps 6–8 as follows:

A 21-aldehyde hydrate (2) is treated with a trialkyl orthoformate such as trimethyl orthoformate, triethyl orthoformate, tri-n-propyl orthoformate and the like in the presence of a strong acid such as perchloric acid, p-toluenesulfonic acid, sulfuric acid and the like to obtain the 3-alkoxy-3,5-dien-21-acetal (B). The reaction is conducted in the presence of an alkanol corresponding to the trialkyl orthoformate employed at a temperature of 50° to 100° C. for a period of 2 to 12 hours.

Treatment of the thus obtained 3-alkoxy compound (B) with a dilute inorganic acid such as hydrochloric acid, sulfuric acid and the like yields the 3-oxo-5-en-21-acetal (C). This reaction is preferably conducted in aqueous acetone at a temperature of 50° to 80° C. for a period of 30 minutes to 4 hours.

Thereafter, the 3-oxo-5-en-21-acetal (C) is treated with a base such as sodium hydroxide, potassium hydroxide, ammonium hydroxide and the like to yield the 3-oxo-4-en-21-acetal (7). This reaction is preferably conducted in a solvent such as methylene chloride/methanol, aqueous acetone or methanol at a temperature of 30° to 60° C. for a period of 30 minutes to 4 hours.

Alternatively, the 3-alkoxy-3,5-dien-21-acetal (B) can be treated with a higher concentration of a strong acid such as hydrochloric acid, perchloric acid, sulfuric acid and the like to yield directly the 3-oxo-4-en-21-acetal (7). This reaction is preferably conducted in aqueous acetone.

For those 21-aldehyde hydrates (2) wherein Z is a double bond and $X^1$ is hydrogen, the reaction conditions of step 6 lead directly to compounds of formula (7).

The 21-hydroxy steroid starting materials (1) used to prepare the 21-acetal and 21-difunctional compounds of the instant invention are available commercially or can be prepared according to known procedures. Information concerning the preparation of 21-hydroxy steroids suitable for use in the preparation of compounds of Formulas (A), (B), and (C) and be obtained, for example for U.S. Pat. Nos. 3,048,581 and 3,126,375; and from Fried et al., J. Am. Chem. Soc., 802, 338 (1958) and Mills et al., J. Am. Chem. Soc., 82, 3399 (1960). Additional information concerning the preparation of 21-hydroxy steroids suitable for use in the preparation of compounds of Formulas (A), (B), and (C) can be found for example, in U.S. Pat. Nos. 2,894,963, 3,013,033 and 3,119,748; and Edwards et al., Proc. Chem. Soc. (London), p. 87 (1959), Edwards et al., J. Am. Chem. Soc., 82, 2318 (1960), and Taub et al., J. Am. Chem. Soc., 80, 4435 (1958).

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLE 1

6α,9α-difluoro-11β,16α,17α,21,21-pentahydroxypregna-1,4-diene-3,20-dione-16,17-acetonide To a slurry of 12.0 g. of 6α,9α-difluro-11β,16α,17α,21-tetrahydroxypregna-1,4-diene-3,20-dione-16,17-acetonide in 130 ml. of dry methanol is added a solution of 0.68 g. of cupric acetate hydrate in 40 ml. methanol. Air is then sparged through the mixture for 2 hours. Thereafter, the mixture is evaporated to dryness and the residue is taken up in ethyl acetate and washed with water and then with a dilute aqueous solution of potassium bicarbonate and then again with water. The solution is evaporated to dryness and the resulting residue is then dissolved in acetone. The acetone solution is diluted with a substantial volume of water whereupon the resulting precipitate is filtered and dried under vacuum to yield 6α,9α-difluoro-11β,16α,17α,21,21-pentahydroxypregna-1,4-diene-3,20-dione-16,17-acetonide.

EXAMPLE 2

6α,9α-difluoro-11β,16α,17α-trihydroxypregna-1,4-diene-3,20,21-trione-16,17-acetonide 6α,9α-difluoro-11β,16α,17α,21,21-pentahydroxypregna-1,4-diene-3,20-dione-16,17-acetonide (4.0 g.) is heated under high vacuum in an oil bath at 100° C. for 1 hour to yield 6α,9α-difluoro-11β,16α,17α-trihydoxypregna-1,4-diene-3,20,21-trione-16,17-acetonide.

EXAMPLE 3

6α,9α-difluoro-11β,16α,17α,21,21-pentahydroxypregna-1,4-diene-3,20-dione-16,17-acetonide-21-methyl ether 6α,9α-difluoro-11β,16α,17α-trihydroxypregna-1,4-3,20,21-trione-16,17-acetonide (obtained above in Example 2) is dissolved in 50 ml. of dry methanol. After stirring for approximately 15 minutes at room temperature the solution color changes from yellow to colorless. The solution is then evaporated and dried at 50° C. under vacuum to yield 6α,9α-difluoro-11β,16α,17α,21,21-pentahydroxypregna-1,4-diene-3,20-dione-16,17-acetonide-21-methyl ether.

Replacing methanol in the above procedure with other lower alkanols, e.g., ethanol, isopropanol, n-butanol, sec-butanol, amyl alcohol etc., is productive of the corresponding 21-aldehyde hemiacetals, for example, 6α,9α-difluoro-11β,16α,17α,21,21-pentahydroxypregna-1,4-diene-3,20-dione-16,17-acetonide-21-ethyl ether, 6α,9α-difluoro-11β,16α,17α,21,21-pentahydroxypregna-1,4-diene-3,20-dione-16,17-acetonide-21-n-propyl ether, 6α,9α-difluoro-11β,16α,17α,21,21-pentahydroxypregna-1,4-diene-3,20-dione-16,17-acetonide-21-isopropyl ether, 6α,9α-difluoro-11β,16α,17α,21,21-pentahydroxypregna-1,4-diene-3,20-dione-16,17-acetonide-21-n-butyl ether, 6α,9α-difluoro-11β,16α,17α,21,21-pentahydroxypregna-1,4-diene-3,20-dione-16,17-acetonide-21-butyl ether, 6α,9α-difluoro-11β,16α,17α,21,21-pentahydroxypregna-1,4-diene-3,20-dione-16,17-acetonide-21-n-amyl ether, and so forth.

EXAMPLE 4

21-chloro-6α,9α-difluoro-11β,16α,17α,21-tetrahydroxypregna-1,4-diene-3,20-dione-16,17-acetonide-21-methyl ether 6α,9α-difluoro-11β,16α,17α,21,21-pentahydroxypregna-1,4-diene-3,20-dione-16,17-acetonide-21-methyl ether (2.5 g.) is dissolved in 100 ml. of dry methylene chloride and 1.2 ml. of triethylamine is added to the solution which is cooled to −15° C. under a nitrogen atmosphere. Methane sulfonyl chloride (1.2 ml.) is then added and the solution is allowed to warm to 0° C. with stirring. After 16 hours at 0° C. there is obtained 21-chloro-6α,9α-difluoro-11β,16α,17α,21-tetrahydroxypregna-1,4-diene-3,20-dione-16,17-acetonide-21-methyl ether, m.p. 207°–213° C. The product can be recovered by evaporation of the solvent or used directly in solution in the next example.

Repeating the above procedure but substituting thionyl bromide for methane sulfonyl chloride is productive of the corresponding 21-bromo-6α,9α-difluoro-11β,16α,17α,21-tetrahydroxypregna-1,4-diene-3,20-dione-16,17-acetonide-21-methyl ether.

In like manner, other 21-halo-21-alkyl ether steroids are prepared, for example:
  21-chloro-6α,9α-difluoro-11β,16α,17α,21-tetrahydroxypregna-1,4-diene-3,20-dione-16,17-acetonide-21-ethyl ether,
  21-chloro-6α,9α-difluoro-11β,16α,17α,21-tetrahydroxypregna-1,4-diene-3,20-dione-16,17-acetonide-21-n-propyl ether,
  21-chloro-6α,9α-difluoro-11β,16α,17α,21-tetrahydroxypregna-1,4-diene-3,20-dione-16,17-acetonide-21-isopropyl ether,
  21-chloro-6α,9α-difluoro-11β,16α,17α,21-tetrahydroxypregna-1,4-diene-3,20-dione-16,17-acetonide-21-n-butyl ether,
  21-chloro-6α,9α-difluoro-11β,16α,17α,21-tetrahydroxypregna-1,4-diene-3,20-dione-16,17-acetonide-21-sec-butyl ether,
  21-chloro-6α,9α-difluoro-11β,16α,17α,21-tetrahydroxypregna-1,4-diene-3,20-dione-16,17-acetonide-21-n-amyl ether,
  21-chloro-6α,9α-difluoro-11β,16α,17α,21-tetrahydroxypregna-1,4-diene-3,20-dione-16,17-acetonide-21-n-hexyl ether,
  21-chloro-6α,9α-difluoro-11β,16α,17α,21-tetrahdroxypregna-1,4-diene-3,20-dione-16,17-acetonide-21-n-heptyl ether,
  21-chloro-6α,9α-difluoro-11β,16α,17α,21-tetrahydroxypregna-1,4-diene-3,20-dione-16,17-acetonide-21-n-octyl ether,
and also the corresponding 21-bromo-21-alkyl ether steroids, e.g.,
  21-bromo-6α,9α-difluoro-11β,16α,17α,21-tetrahydroxypregna-1,4-diene-3,20-dione-16,17-acetonide-21-ethyl ether,
  21-bromo-6α,9α-difluoro-11β,16α,17α,21-tetrahydroxypregna-1,4-diene-3,20-dione-16,17-acetonide-21-n-propyl ether,
  21-bromo-6α,9α-difluoro-11β,16α,17α,21-tetrahydroxypregna-1,4-diene-3,20-dione-16,17-acetonide-21-isopropyl ether,
  21-bromo-6α,9α-difluoro-11β,16α,17α,21-tetrahydroxypregna-1,4-diene-3,20-dione-16,17-acetonide-21-n-butyl ether,
  21-bromo-6α,9α-difluoro-11β,16α,17α,21-tetrahydroxypregna-1,4-diene-3,20-dione-16,17-acetonide-21-sec-butyl ether,
  21-bromo-6α,9α-difluoro-11β,16α,17α,21-tetrahydroxypregna-1,4-diene-3,20-dione-16,17-acetonide-21-n-amyl ether,
  21-bromo-6α,9α-difluoro-11β,16α,17α,21-tetrahydroxypregna-1,4-diene-3,20-dione-16,17-acetonide-21-n-hexyl ether,
  21-bromo-6α,9α-difluoro-11β,16α,17α,21-tetrahydroxypregna-1,4-diene-3,20-dione-16,17-acetonide-21-n-heptyl ether, and
  21-bromo-6α,9α-difluoro-11β,16α,17α,21-tetrahydroxypregna-1,4-diene-3,20-dione-16,17-acetonide-21-octyl ether.

EXAMPLE 5

6α,9α-difluoro-11β,16α,17α,21,21-pentahydroxypregna-1,4-diene-3,20-dione-16,17-acetonide-21,21-bis-methyl ether To the methylene chloride solution of 21-chloro-6α,9α-difluoro-11β,16α,17α,21-tetrahydroxypregna-1,4-diene-3,20-dione-16,17-acetonide-21-methyl ether, obtained in Example 4, is added 200 ml. of dry methanol and the methylene chloride is then removed by distillation. The resulting solution is heated under nitrogen at 60° C. while a 0.5 normal solution of sodium methoxide in methanol is added dropwise at a rate sufficient to maintain a pH of 8. After approximately 4 hours the reaction is complete whereupon the reaction mixture is concentrated to approximately 50 ml. by evaporation. The the resultant precipitates is filtered, washed with water and vacuum dried. The precipitate is recrystallized from a mixture of methanol and methylene chloride to yield 6α,9α-difluoro-11β,17α,17α,21,21-pentahydroxypregna-1,4-diene-3,20-dione-16,17-acetonide-21,21-bis-methyl ether, m.p. 291°–292° C.

Repeating the above procedure, but substituting other alkoxides for sodium methoxide and using an alkanol corresponding to the alkoxide used is productive of the corresponding 21-methyl-21-alkyl ether steroids, for example,
  6α,9α-difluoro-11β,16α,17α,21,21-pentahydroxypregna-1,4-diene-3,20-dione-16,17-acetonide-21-methyl-21-ethyl ether,
  6α,9α-difluoro-11β,16α,17α,21,21-pentahydroxypregna-1,4-diene-3,20-dione-16,17-acetonide-21-methyl-21-n-propyl ether,
  6α,9α-difluoro-11β,16α,17α,21,21-pentahydroxypregna-1,4-diene-3,20-dione-16,17-acetonide-21-methyl-21-n-isopropyl ether,
  6α,9α-difluoro-11β,16α,17α,21,21-pentahydroxypregna-1,4-diene-3,20-dione-16,17-acetonide-21-methyl-21-n-butyl ether,
  6α,9α-difluoro-11β,16α,17α,21,21-pentahydroxypregna-1,4-diene-3,20-dione-16,17-acetonide-21-methyl-21-sec-butyl ether,
  6α,9α-difluoro-11β,16α,17α,21,21-pentahydroxypregna-1,4-diene-3,20-dione-16,17-acetonide-21-methyl-21-n-amyl ether,
  6α,9α-difluoro-11β,16α,17α,21,21-pentahydroxypregna-1,4-diene-3,20-dione-16,17-acetonide-21-methyl-21-n-hexyl ether,
  6α,9α-difluoro-11β,16α,17α,21,21-pentahydroxypregna-1,4-diene-3,20-dione-16,17-acetonide-21-methyl-21-n-heptyl ether, and
  6α,9α-difluoro-11β,16α,17α,21,21-pentahydroxypregna-1,4-diene-3,20-dione-16,17-acetonide-21-methyl-21-n-octyl ether, empimer A m.p. 189°–193° C.; epimer B m.p. 113°–116° C.

In like manner, other 21,21-bis-alkyl ether steroids and 21-mixed alkyl ether steroids are pepared, for example
  6α,9α-difluoro-11β,16α,17α,21,21-pentahydroxypregna-1,4-diene-3,20-dione-16,17-acetonide-21,21-bis-ethyl ether, m.p. 269°–275° C.,
  6α,9α-difluoro-11β,16α,17α,21,21-pentahydroxypregna-1,4-diene-3,20-dione-16,17-acetonide-21,21-bis-n-propyl ether, m.p. 244°–248° C., 6α,9α-difluoro-11β,16α,17α,21,21-pentahydroxy-pregna-1,4-diene-3,20-dione-16,17-acetonide-21,21-bis-isopropyl ether, 6α,9α-difluoro-11β,16α,17α,21,21-pentahydroxy-pregna-1,4-diene-3,20-dione-16,17-acetonide-21,21-bis-n-butyl ether, 6α,9α-difluoro-11β,16α,17α,21,21-pentahydroxy-pregna-1,4-diene-3,20-dione-16,17-acetonide-21,21-bis-sec-butyl ether, 6α,9α-difluoro-11β,16α,17α,21,21-pentahydroxy-pregna-1,4-diene-3,20-dione-16,17-acetonide-21,21-bis-n-amyl ether, 6α,9α-difluoro-11β,16α,17α,21,21-pentahydroxy-pregna-1,4-diene-3,20-dione-16,17-acetonide-21,21-bis-n-hexyl ether, 6α,9α-difluoro-11β,16α, 17α,21,21-pentahydroxy-pregna-1,4-diene-3,20-dione-16,17-acetonide-21,21-bis-n-heptyl ether, 6α,9α-difluoro-11β,16α, 17α,21,21-pentahydroxy-pregna-1,4-diene-3,20-dione-16,17-acetonide-21,21-bis-n-octyl ether, 6α,9α-difluoro-11β,16α,17α,21,21-pentahydroxy-pregna-1,4-diene-3,20-dione-16,17-acetonide-21-ethyl-21-n-propyl ether, 6α,9α-difluoro-11β,16α,17α,21,21-pentahydroxy-pregna-1,4-diene-3,20-dione-16,17-acetonide-21-ethyl-21-n-butyl ether, 6α,9α-difluoro-11β,16α,17α,21,21-pentahydroxy-pregna-1,4-diene-3,20-dione-16,17-acetonide-21-n-propyl-21-n-butyl ether, 6α,9α-difluoro-11β,16α,17α-21,21-pentahydroxy-pregna-1,4-diene-3,20-dione-16,17-acetonide-21-ethyl-21-n-hexyl ether, 6α,9α-difluoro-11β,16α,17α,21,21-pentahydroxy-pregna-1,4-diene-3,20-dione-16,17-acetonide-21-ethyl-21-n-heptyl ether, 6α,9α-difluoro-11β,16α,17α,21,21-pentahydroxy-pregna-1,4-diene-3,20-dione-16,17-acetonide-21-ethyl-21-n-octyl ether, 6α,9α-difluoro-11β,16α,17α,21,21-pentahydroxy-pregna-1,4-diene-3,20-dione-16,17-acetonide-21-n-propyl-21-n-amyl ether, 6α,9α-difluoro-11β,16α,17α,21,21-pentahydroxy-pregna-1,4-diene-3,20-dione-16,17-acetonide-21-isopropyl-21-n-hexyl ether, 6α,9α-difluoro-11β,16α,17α,21,21-pentahydroxy-pregna-1,4-diene-3,20-dione-16,17-acetonide-21-n-propyl-21-n-heptyl ether, 6α,9α-difluoro-11β,16α,17α,21,21-pentahydroxy-pregna-1,4-diene-3,20-dione-16,17-acetonide-21-n-propyl-21-n-octyl ether, 6α,9α-difluoro-11β,16α,17α,21,21-pentahydroxy-pregna-1,4-diene-3,20-dione-16,17-acetonide-21-n-amyl-21-n-hexyl ether, 6α,9α-difluoro-11β,16α,17α,21,21-pentahydroxy-pregna-1,4-diene-3,20-dione-16,17-acetonide-21-n-amyl-21-n-heptyl ether, 6α,9α-difluoro-11β,16α,17α,21,21-pentahydroxy-pregna-1,4-diene-3,20-dione-16,17-acetonide-21-n-amyl-21-n-octyl ether, 6α,9α-difluoro-11β,16α,17α,21,21-pentahydroxy-pregna-1,4-diene-3,20-dione-16,17-acetonide-21-n-heptyl-21-n-hexyl ether, and 6α,9α-difluoro-11β,16α,17α,21,21-pentahydroxy-pregna-1,4-diene-3,20-dione-16,17-acetonide-21-n-hexyl-21-n-octyl ether,

EXAMPLE 6

21-azido-6α,9α-difluoro-11β,16α,17α,21-tetrahydroxypregna-1,4-diene-3,20-dione-16,17-acetonide-21-methyl ether To a solution of 100 mg. of 21-chloro-6α,9α-difluoro-11β,16α,17α,21-tetrahydroxypregna-1,4-diene-3,20-dione-16,17-acetonide-21-methyl ether in 50 ml. of methylene chloride (obtained in Example 4) is added 10 ml. of dry dimethylformamide and the methylene chloride is then removed from the solution by distillation. Sodium azide (40 mg.) is added to the resulting solution and the mixture is stirred at room temperature for 16 hours. The reaction mixture is then poured into water and the resulting mixture extracted with chloroform. The chloroform extracts are washed with water and dried over sodium sulfate, and evaporated to dryness. The resulting impure product is chromatographed on a silica GF plate (1 m. × 20 cm. × 0.5 mm.) which is developed twice with 12% acetone in hexane. The product is removed from the plate to yield 21-azido-6α,9α-difluoro-11β,16α,17α,21-tetrahydroxypregna-1,4-diene-3,20-dione-16,17-acetonide-21-methyl ether, m.p. 220°–222° C.

In like manner, other 21-azido-21-alkyl ether steroids are prepared, for example 21-azido-6α,9α-difluoro-11β,16α,17α,21-tetrahydroxypregna-1,4-diene-3,20-dione-16,17-acetonide-21-ethyl ether, 21-azido-6α,9α-difluoro-11β,16α,17α,21-tetrahydroxypregna-1,4-diene-3,20-dione-16,17-acetonide-21-n-propyl ether, 21-azido-6α,9α-difluoro-11β,16α,17α,21-tetrahydroxypregna-1,4-diene-3,20-dione-16,17-acetonide-21-isopropyl ether, 21-azido-6α,9α-difluoro-11β,16α,17α,21-tetrahydroxypregna-1,4-diene-3,20-dione-16,17-acetonide-21-n-butyl ether, 21-azido-6α,9α-difluoro-11β,16α,17α,21-tetrahydroxypregna-1,4-diene-3,20-dione-16,17-acetonide-21-sec-butyl ether, 21-azido-6α,9α-difluoro-11β,16α,17α,21-tetrahydroxypregna-1,4-diene-3,20-dione-16,17-acetonide-21-n-amyl ether, 21-azido-6α,9α-difluoro-11β,16α,17α,21-tetrahydroxypregna-1,4-diene-3,20-dione-16,17-acetonide-21-n-hexyl ether, 21-azido-6α,9α-difluoro-11β,16α,17α,21-tetrahydroxypregna-1,4-diene-3,20-dione-16,17-acetonide-21-n-heptyl ether, and 21-azido-6α,9α-difluoro-11β,16α,17α,21-tetrahydroxypregna-1,4-diene-3,20-dione-16,17-acetonide-21-n-octyl ether.

EXAMPLE 7

6α,9α-difluoro-11β,16α,17α,21-tetrahydroxy-21-thiocyanopregna-1,4-diene-3,20-dione-16,17-acetonide-21-methyl ether To a solution of 160 mg. of 21-chloro-6α,9α-difluoro-11β,16α,17α,21-tetrahydroxypregna-1,4-diene-3,20-dione-16,17-acetonide-21-methyl ether in 80 ml. of methylene chloride (obtained in Example 4) is added 30 ml. of dry dimethylformamide and the methylene chloride is removed by distillation. Thereafter, 265 mg. of potassium thiocyanate is added and the mixture is heated under nitrogen at 70° C. After 4 hours the mixture is poured into water and the resulting aqueous mixture extracted with ethyl acetate. The organic phase is washed with water, dried over sodium sulfate and evaporated to dryness. The product is then chromatographed on a silica GF plate (1 m. × 20 cm. × 0.5 mm.) which is developed with 15% acetone and hexane. The product is removed from the plate to yield 6α,9α-difluoro-11β,16α,17α,21-tetrahydroxy-21-thiocyanopregna-1,4-diene-3,20-dione-16,17-acetonide-21-methyl ether, m.p. 233°–237° C.

In like manner, other 21-thiocyano-21-alkyl ether steroids are prepared, for example 6α,9α-difluoro-11β,16α,17α,21-tetrahydroxy-21-thiocyanopregna-1,4-diene-3,20-dione-16,17-acetonide-21-ethyl ether, 6α,9α-difluoro-11β,16α,17α,21-tetrahydroxy-21-thiocyanopregna-1,4-diene-3,20-dione-16,17-acetonide-21-n-propyl ether, 6α,9α-difluoro-11β,16α,17α,21-tetrahydroxy-21-thiocyanopregna-1,4-diene-3,20-dione-16,17-acetonide-21 isopropyl ether, 6α,9α-difluoro-11β,16α,17α,21-tetrahydroxy-21-thiocyanopregna-1,4-diene-3,20-dione-16,17-acetonide-21-n-butyl ether, 6α,9α-difluoro-11β,16α,17α,21-tetrahydroxy-21-thiocyanopregna-1,4-diene-3,20-dione-16,17-acetonide-21-sec-butyl ether, 6α,9α-difluoro-11β,16α,17α,21-tetrahydroxy-21-thiocyanopregna-1,4-diene-3,20-dione-16,17-acetonide-21-n-amyl ether, 6α,9α-difluoro-11β,16α,17α,21-tetrahydroxy-21-thiocyanopregna-1,4-diene-3,20-dione-16,17-acetonide-21-n-hexyl ether, 6α,9α-difluoro-11β,16α,17α,21-tetrahydroxy-21-thiocyanopregna-1,4-diene-3,20-dione-16,17-acetonide-21-n-heptyl ether, and 6α,9α-difluoro-11β,16α,17α,21-tetrahydroxy-21-thiocyanopregna-1,4-diene-3,20-dione-16,17-acetonide-21-n-octyl ether.

EXAMPLE 8

21-Cyano-6α,9α-difluoro-11β,16α,17α,21-tetrahydroxypregna-1,4-diene-3,20-dione-16,17-acetonide-21-methyl ether To a solution of 160 mg. of 21-chloro-6α,9α-difluoro-11β,16α,17α,21-tetrahydroxypregna-1,4-diene-3,20-dione-16,17-acetonide-21-methyl ether in 80 ml. of methylene chloride (obtained in Example 4) is added 30 ml. of dry dimethylformamide and the methylene chloride is removed by distillation. Thereafter, 200 mg. of sodium cyanide is added and the mixture is heated under nitrogen at 70° C. After 4 hours the reaction mixture is poured into water and the product extracted with ethyl acetate. The organic phase is then washed with water, dried over sodium sulfate and evaporated to dryness. The residue is purified by preparative thin layer chromatography to yield 21-cyano-6α,9α-difluoro-11β,16α,17α,21-tetrahydroxypregna-1,4-diene-3,20-dione-16,17-acetonide-21-methyl ether, epimer A m.p. 272°–275° C.; epimer B m.p. 219°–222° C.

In like manner, other 21-cyano-21-alkyl ether steroids are prepared, for example 21-cyano-6α,9α-difluoro-11β,16α,17α,21-tetrahydroxypregna-1,4-diene-3,20-dione-16,17-acetonide-21-ethyl ether, 21-cyano-6α,9α-difluoro-11β,16α,17α,21-tetrahydroxypregna-1,4-diene-3,20-dione-16,17-acetonide-21-n-propyl ether, 21-cyano-6α,9α-difluoro-11β,16α,17α,21-tetrahydroxypregna-1,4-diene-3,20-dione-16,17-acetonide-21-isopropyl ether, 21-cyano-6α,9α-difluoro-11β,16α,17α,21-tetrahydroxypregna-1,4-diene-3,20-dione-16,17-acetonide-21-n-butyl ether, 21-cyano-6α,9α-difluoro-11β,16α,17α,21-tetrahydroxypregna-1,4-diene-3,20-dione-16,17-acetonide-21-sec-butyl ether, 21-cyano-6α,9α-difluoro-11β,16α,17α,21-tetrahydroxypregna-1,4-diene-3,20-dione-16,17-acetonide-21-n-amyl ether, 21-cyano-6α,9α-difluoro-11β,16α,17α,21-tetrahydroxypregna-1,4-diene-3,20-dione-16,17-acetonide-21-n-hexyl ether, 21-cyano-6α,9α-difluoro-11β,16α,17α,21-tetrahydroxypregna-1,4-diene-3,20-dione-16,17-acetonide-21-n-heptyl ether, and 21-cyano-6α,9α-difluoro-11β,16α,17α,21-tetrahydroxypregna-1,4-diene-3,20-dione-16,17-acetonide-21-n-octyl ether.

EXAMPLE 9

6α,9α-difluoro-11β,16α,17α,21-tetrahydroxy-21-thiophenylpregna-1,4-diene-3,20-dione-16,17-acetonide-21-methyl ether To a solution of 140 mg. of 21-chloro-6α,9α-difluoro-11β,16α,17α,21-tetrahydroxypregna-1,4-diene-3,20-dione-16,17-acetonide-21-methyl ether in 70 ml. of methylene chloride (obtained in Example 4) is added 30 ml. of acetone and the methylene chloride is removed by distillation. Approximately 0.5 g. of sodium thiophenylate is added and the mixture is stirred at room temperature for 16 hours. The reaction mixture is then poured into water and the product extracted with ethyl acetate. The combined extracts are washed with water, dried over sodium sulfate and evaporated to dryness. The resulting impure product is chromatographed on a silica GF plate (1 m. × 20 cm. × 0.5 mm.) which is developed with 20% ethyl acetate in benzene to yield 6α,9α-difluoro-11β,16α,17α,21-tetrahydroxy-21-thiophenyl-pregna-1,4-diene-3,20-dione-16,17-acetonide-21-methyl ether, epimer A m.p. 247°–250° C., epimer B m.p. 219°–222° C.

In like manner, other 21-thiophenyl-21-alkyl ether steroids are prepared, for example 6α,9α-difluoro-11β,16α,17α,21-tetrahydroxy-21-thiophenylpregna-1,4-diene-3,20-dione-16,17-acetonide-21-ethyl ether, 6α,9α-difluoro-11β,16α,17α,21-tetrahydroxy-21-thiophenylpregna-1,4-diene-3,20-dione-16,17-acetonide-21-n-propyl ether, 6α,9α-difluoro-11β,16α,17α,21-tetrahydroxy-21-thiophenylpregna-1,4-diene-3,20-dione-16,17-acetonide-21-isopropyl ether, 6α,9α-difluoro-11β,16α,17α,21-tetrahydroxy-21-thiophenylpregna-1,4-diene-3,20-dione-16,17-acetonide-21-n-butyl ether, 6α,9α-difluoro-11β,16α,17α,21-tetrahydroxy-21-thiophenylpregna-1,4-diene-3,20-dione-16,17-acetonide-21-sec-butyl ether, 6α,9α-difluoro-11β,16α,17α,21-tetrahydroxy-21-thiophenylpregna-1,4-diene-3,20-dione-16,17-acetonide-21-n-amyl ether, 6α,9α-difluoro-11β,16α,17α,21-tetrahydroxy-21-thiophenylpregna-1,4-diene-3,20-dione-16,17-acetonide-21-n-hexyl ether, 6α,9α-difluoro-11β,16α,17α,21-tetrahydroxy-21-thiophenylpregna-1,4-diene-3,20-dione-16,17-acetonide-21-n-heptyl ether, and 6α,9α-difluoro-11β,16α,17α,21-tetrahydroxy-21-thiophenylpregna-1,4-diene-3,20-dione-16,17-acetonide-21-n-octyl ether.

EXAMPLE 10

6α,9α-difluoro-11β,16α,17α,21-tetrahydroxy-21-thioethylpregna-1,4-diene-3,20-dione-16,17-acetonide-21-methyl ether To a solution of 140 mg. of 21-chloro-6α,9α-difluoro-11β,16α,17α,21-tetrahydroxypregna-1,4-diene-3,20-dione-16,17-acetonide-21-methyl ether in 70 ml. of methylene chloride (obtained in Example 4) is added 30 ml. of acetone and the methylene chloride is removed by distillation. Approximately 0.5 g. of sodium thioethylate is added and the mixture is stirred at room temperature for a period of 16 hours. The reaction mixture is then poured into water and the product extracted with ethyl acetate. The combined extracts are washed with water, dried over sodium sulfate and evaporated to dryness. The resulting impure product is chromatographed on a silica GF plate (1 m. × 20 cm. × 0.5 mm.) which is developed twice with 12% acetone in benzene to yield 6α,9α-difluoro-11β,16α,17α,21-tetrahydroxy-21-thioethyl-pregna-1,4-diene-3,20-dione-16,17-acetonide-21-methyl ether, epimer A m.p. 280°–282° C., epimer B m.p. 254°–256° C.

In like manner, other 21-thioalkyl-21-alkyl ether steroids are prepared, for example 6α,9α-difluoro-11β,16α,17α,21-tetrahydroxy-21-thiomethylpregna-1,4-diene-3,20-dione-16,17-acetonide-21-methyl ether, 6α,9α-difluoro-11β,16α,17α,21tetrahydroxy-21-thio-n-butyl-pregna-1,4-diene-3,20-dione-16,17-acetonide-21-n-butyl ether, 6α,9α-difluoro-11β,16α,17α,21-tetrahydroxy-21-thio-n-hexyl-pregna-1,4-diene-3,20-dione-16,17-acetonide-21-n-hexyl ether, 6α,9α-difluoro-11β, 16α,17α,21-tetrahydroxy-21-thiomethylpregna-1,4-diene-3,20-dione-16,17-acetonide-21-n-propyl ether, 6α,9α-difluoro-11β,16α,17α,21-tetrahydroxy-21-thiomethylpregna-1,4-diene-3,20-dione-16,17-acetonide-21-n-octyl ether, 6α,9α-difluoro-11β,16α,17α,21-tetrahydroxy-21-thioethylpregna-1,4-diene-3,20-dione-16,17-acetonide-21-n-hexyl ether, 6α,9α-difluoro-11β,16α,17α,21-tetrahydroxy-21-thio-n-octyl-pregna-1,4-diene-3,20-dione-16,17-acetonide-21-methyl ether.

EXAMPLE 11

6α,9α-difluoro-11β,16α,17α,21,21-pentahydroxypregna-1,4-diene-3,20-dione-16,17-acetonide-21,21-bis-methyl ether a. 6α,9α-difluoro-11β,16α,17α,21,21-pentahydroxypregna-1,4-diene-3,20-dione-16,17-acetonide (300 mg.) is dissolved in a mixture of 8 ml. of trimethyl orthoformate and 2 ml. of methanol. Two drops of concentrated perchloric acid is then added to the mixture which is stirred and heated at 50° C. under nitrogen. After 2 hours, the reaction mixture is diluted with ethyl acetate, washed with water until neutral, dried over sodium sulfate and evaporated to dryness to yield 6,9α-difluoro-3,11β,16α,17α,21,21-hexahydroxypregna-1,3,5-triene-20-one-16,17-acetonide-3,21,21-tris-methyl ether, m.p. 168°–176° C.

b. 30 mg. of the crude triene obtained above is dissolved in 5 ml. of acetone and 2 ml. of water and 1 drop of concentrated HCl is added. After refluxing for 30 minutes under nitrogen, water is added to the reaction mixture and the acetone was removed by distillation. The resulting precipitate is filtered off and dried under vacuum to yield 6,9α-difluoro-11β,16α,17α,21,21-pentahydroxypregna-1,5-diene-3,20-dione-16,17-acetonide-21,21-bis-methyl ether, m.p. 267°–270° C.

c. 100 mg. of the crude 1,5-diene obtained above is dissolved in 15 ml. of a 2:1 mixture of methylene chloride and methanol and 1 drop of aqueous 3N sodium hydroxide is added. After 15 minutes at room temperature, the reaction mixture is diluted with ethyl acetate. The organic phase is then separated, washed with water and dried over sodium sulfate. The product is recrystallized from a mixture of methanol and methylene chloride to yield 6α,9α-difluoro-11β,16α,17α,21,21-pentahydroxypregna-1,4-diene-3,20-dione-16,17-acetonide-21,21-bis-methyl ether.

Repeating the above procedures but substituting other alkyl orthoformates in paragraph (a) for trimethyl orthoformate, e.g. triethyl orthoformate, tri-n-propyl orthoformate, tri-n-butyl orthoformate, and so forth is productive of the corresponding 1,4-diene-3,20-dione-21,21-bis-alkyl ether steroids and also the 1,3,5-trien-20-dione-3,21,21-trialkyl ether steroids, for example 6α,9α-difluoro-3β,11β,16α,17α,21,21-hexyhydroxypregna-1,3,5-trien-20-dione-16,17-acetonide-3,21,21-tris-ethyl ether, 6α,9α-difluoro-3β,11β,16α,17α,21,21-hexahydroxypregna-1,3,5-trien-20-dione-16,17-acetonide-3,21,21-tris-n-propyl ether, 6α,9α-difluoro-3β,11β,16α,17α,21,21-hexahydroxypregna-1,3,5-trien-20-dione-16,17-acetonide-3,21,21-tris-n-butyl ether, and so forth, and also the 1,5-diene-3,20-dione-21,21-bis-alkyl ether steroids for example 6α,9α-difluoro-11β,16α,17α,21,21-pentahydroxypregna-1,5-dien-3,20-dione-16,17-acetonide-21,21-bis-ethyl ether, 6α,9α-difluoro-11β,16α,17α,21,21-pentahydroxypregna-1,5-dien-3,20-dione-16,17-acetonide-21,21-bis-n-propyl ether, 6α,9α-difluoro-11β,16α,17α,21,21-pentahydroxypregna-1,5-dien-3,20-dione-16,17-acetonide-21,21-bis-n-butyl ether, and so forth.

EXAMPLE 12

In similar manner to the procedures of Examples 1–10, using reactants as dictated by the particular 21-acetal or 21-mixed acetal desired, the following compounds are prepared:

21-chloro-6α-fluoro-11β,16α,17α,21-tetrahydroxypregna-1,4-diene-3,20-dione-16,17-acetonide-21-methyl ether, 21-chloro-6α,9α-difluoro-11β,16α,17α,21-tetrahydroxypregn-4-ene-3,20-dione-16,17-acetonide-21-methyl ether, 21-chloro-6α-fluoro-11β,16α,17α,21-tetrahydroxypregn-4-ene-3,20-dione-16,17-acetonide-21-methyl ether, 9α,11β,21-trichloro-6α-fluoro-16α,17α,21-trihydroxypregna-1,4-diene-3,20-dione-16,17-acetonide-21-methyl ether, 9α,21-dichloro-6α-fluoro-11β,16α,17α,21-tetrahydroxypregna-1,4-diene-3,20-dione-16,17-acetonide-21-methyl ether, decomp. 180°–190° C., 21-chloro-6α,9α-difluoro-11β,17α,21-trihydroxy-16α-methylpregna-1,4-diene-3,20-dione-21-methyl ether, 21-chloro-6α,9α-difluoro-11β,17α,21-trihydroxy-16α-methylpregna-1,4-diene-3,20-dione-17-caprylate-21-methyl ether, 21-chloro-6α,9α-difluoro-11β,17α,21-trihydroxy-16α-methylpregna-1,4-diene-3,20-dione-17-benzoate-21-methyl ether, 21-chloro-9α-fluoro-11β,17α,21-trihydroxy-16β-methylpregna-1,4-diene-3,20-dione-17-valerate-21-methyl ether, 21-chloro-9α-fluoro-11β,17α,21-trihydroxy-16β-methylpregn-4-ene-3,20-dione-21-methyl ether, 21-chloro-9α-fluoro-11β,16α,17α,21-tetrahydroxypregna-1,4-diene-3,20-dione-16,17-acetonide-21-methyl ether, 21-chloro-6α,9α-difluoro-11β,17α,21-trihydroxy-16α-methylpregna-1,4-diene-3,20-dione-17-acetate-21-methyl ether, 21-chloro-11β,16α,17α,21-tetrahydroxypregn-4-ene-3,20-dione-16,17-acetonide-21-methyl ether, 21-chloro-11β,16α,17α,21-tetrahydroxypregna-1,4-diene-3,20-dione-16,17-acetonide-21-methyl ether, 6α,21-dichloro-11β,16α,17α-21-tetrahydroxypregn-4-ene-3,20-dione-16,17-acetonide-2-methyl ether, 21-chloro-6α-fluoro-11β,16α,17α,21-tetrahydroxypregna-1,4-diene-3,20-dione-16,17-acetonide-21-ethyl ether, 21-chloro-6α,9α-difluoro-11β,16α,17α,21-tetrahydroxypregn-4-ene-3,20-dione-16,17-acetonide-21-ethyl ether, 21-chloro-6α-fluoro-11β,16α,17α,21-tetrahydroxypregn-4-ene-3,20-dione-16,17-acetonide-21-ethyl ether, 9α,11β,21-trichloro-6α-fluoro-16α,17α,21-trihydroxypregna-1,4-diene-3,20-dione-16,17-acetonide-21-ethyl ether, 9α,21-dichloro-6α-fluoro-11β,16α,17α,21-tetrahydroxypregna-1,4-diene-3,20-dione-16,17-acetonide-21-ethyl ether, 21-chloro-6α,9α-difluoro-11β,17α,21-trihydroxy-16α-methylpregna-1,4-diene-3,20-dione-21-ethyl ether, 21-chloro-6α,9α-difluoro-11β,17α,21-trihydroxy-16α-methylpregna-1,4-diene-3,20-dione-17-caprylate-21-ethyl ether, 21-chloro-6α,9α-difluoro-11β,17α,21-trihydroxy-16α-methylpregna-1,4-diene-3,20-dione-17-benzoate-21-ethyl ether, 21-chloro-9α-fluoro-11β,17α,21-trihydroxy-16β-methylpregna-1,4-diene-3,20-dione-17-valerate-21-ethyl ether, 21-chloro-9α-fluoro-11β,17α,21-trihydroxy-16β-methylpregn-4-ene-3,20-dione-21-ethyl ether, 21-chloro-9α-fluoro-11β,16α,17α,21-tetrahydroxypregna-1,4-diene-3,20-dione-16,17-acetonide-21-ethyl ether, 21-chloro-6α,9α-difluoro-11β,17α,21-trihydroxy-16α-methylpregna-1,4-diene-3,20-dione-17-acetate-21-ethyl ether, 21-chloro-11β,16α,17α,21-tetrahydroxypregn-4-ene-3,20-dione-16,17-acetonide-21-ethyl ether, 21-chloro-11β,16α,17α,21-tetrahydroxypregna-1,4-diene-3,20-dione-16,17-acetonide-21-ethyl ether, 6α,21-dichloro-11β,16α,17α,21-tetrahydroxypregn-4-ene-3,20-dione-16,17-acetonide-21-ethyl ether, 21-chloro-6α-fluoro-11β,16α,17α,21-tetrahydroxypregna-1,4-diene-3,20-dione-16,17-acetonide-21-n-amyl ether, 21-chloro-6α,9α-difluoro-11β,16α,17α,21-tetrahydroxypregn-4-ene-3,20-dione-16,17-acetonide-21-n-hexyl ether, 21-chloro-6α-fluoro-11β,16α,17α,21-tetrahydroxypregn-4-ene-3,20-dione-16,17-acetonide-21-n-octyl ether, 9α,11β,21-trichloro-6α-fluoro-16α,17α,21-trihydroxypregna-1,4-diene-3,20-dione-16,17-acetonide-21-isopropyl ether, 9α,21-dichloro-6α-fluoro-11β,16α,17α,21-tetrahydroxypregna-1,4-diene-3,20-dione-16,17-acetonide-21-n-butyl ether, 21-chloro-6α,9α-difluoro-11β,17α,21-trihydroxy-16α-methylpregna-1,4-diene-3,20-dione-21-n-propyl ether, 21-chloro-6α,9α-difluoro-11β,17α,21-trihydroxy-16α-methylpregna-1,4-diene-3,20-dione-17-caprylate-21-n-propyl ether, 21-chloro-6α,9α-difluoro-11β,17α,21-trihydroxy-16α-methylpregna-1,4-diene-3,20-dione-17-benzoate-21-n-amyl ether, 21-chloro-9α-fluoro-11β,17α,21-trihydroxy-16β-methylpregna-1,4-diene-3,20-dione-17-valerate-21-n-amyl ether, 21-chloro-9α-fluoro-11β,17α,21-trihydroxy-16β-methylpregn-4-ene-3,20-dione-21-n-butyl ether, 21-chloro-9α-fluoro-11β,16α,17α,21-tetrahydroxypregna-1,4-diene-3,20-dione-16,17-acetonide-21-n-propyl ether, 21-chloro-6α,9α-difluoro-11β,17α,21-trihydroxy-16α-methylpregna-1,4-diene-3,20-dione-17-acetate-21-n-hexyl ether, 21-chloro-11β,16α,17α,21-tetrahydroxypregn-4-ene-3,20-dione-16,17-acetonide-21-n-octyl ether, 21-chloro-11β,16α,17α,21-tetrahydroxypregna-1,4-diene-3,20-dione-16,17-acetonide-21-n-heptyl ether, 21-bromo-6α-fluoro-11β,16α,17α,21-tetrahydroxypregna-1,4-diene-3,20-dione-16,17-acetonide-21-methyl ether, 21-bromo-6α,9α-difluoro-11β,16α,17α,21-tetrahydroxypregn-4-ene-3,20-dione-16,17-acetonide-21-n-propyl ether, 21-bromo-6α-fluoro-11β,16α,17α,21-tetrahydroxypregn-4-ene-3,20-dione-16,17-acetonide-21-ethyl ether, 21-bromo-9α,11β-dichloro-6α-fluoro-16α,17α,21-trihydroxypregna-1,4-diene-3,20-dione-16,17-acetonide-21-n-propyl ether, 21-bromo-9α-chloro-6α-fluoro-11β,16α,17α,21-tetrahydroxypregna-1,4-diene-3,20-dione-16,17-acetonide-21-methyl ether, 21-bromo-6α,9α-difluoro-11β,17α,21-trihydroxy-16α-methylpregna-1,4-diene-3,20-dione-21-n-propyl ether, 21-bromo-6α,9α-difluoro-11β,17α,21-trihydroxy-16α-methylpregna-1,4-diene-3,20-dione-17-caprylate-21-methyl ether, 21-bromo-6α,9α-difluoro-11β,17α,21-trihydroxy-16α-methylpregna-1,4-diene-3,20-dione-17-benzoate-21-methyl ether, 21-bromo-9α-fluoro-11β,17α,21-trihydroxy-16β-methylpregna-1,4-diene-3,20-dione-17-valerate-21-ethyl ether, 21-bromo-9α-fluoro-11β,17α,21-trihydroxy-16β-methylpregn-4-ene-3,20-dione -21-isopropyl ether, 21-bromo-9α-fluoro-11β,16α,17α,21-tetrahydroxypregna-1,4-diene-3,20-dione-16,17-acetonide-21-methyl ether, 21-bromo-6α,9α-difluoro-11β,17α,21-trihydroxypregna-1,4-diene-3,20-dione-17-acetate-21-n-propyl ether, 21-bromo-11β,16α,17α,21-tetrahydroxypregn-4-ene-3,20-dione-16,17-acetonide-21-ethyl ether, 21-bromo-11β,16α,17α,21-tetrahydroxypregna-1,4-diene-3,20-dione-16,17-acetonide-21-n-propyl ether, 21-bromo-6α-fluoro-11β,16α,17α,21-tetrahydroxypregna-1,4-diene-3,20-dione-16,17-acetonide-21-n-amyl ether, 21-bromo-6α-fluoro-11β,16α,17α,21-tetrahydroxypregn-4-ene-3,20-dione-16,17-acetonide-21-n-hexyl ether, 21-bromo-9α-chloro-6α-fluoro-11β,16α,17α,21-tetrahydroxypregna-1,4-diene-3,20-dione-16,17-acetonide-21-n-octyl ether, 21-bromo-9α-fluoro-11β,17α,21-trihydroxy-16β-methylpregna-1,4-diene-3,20-dione-17-valerate-21-n-heptyl ether, 21-bromo-9α-fluoro-11β,16α,17α,21-tetrahydroxypregna-1,4-diene-3,20-dione-16,17-acetonide-21-n-amyl ether, 21-bromo-11β,16α,17α,21-tetrahydroxypregn-4-ene-3,20-dione-16,17-acetonide-21-n-octyl ether, 6α-fluoro-11β,16α,17α,21,21-pentahydroxypregna-1,4-diene-3,20-dione-16,17-acetonide-21,21-bis-methyl ether, m.p. 297°–299° C., 6α,9α-difluoro-11β,16α,17α,21,21-pentahydroxypregn-4-ene-3,20-dione-16,17-acetonide-21,21-bis-methyl ether, m.p. 246°–250° C., 6α-fluoro-11β,16α,17α,21,21-pentahydroxypregn-4-ene-3,20-dione-16,17-acetonide-21,21-bis-methyl ether, m.p. 270°–273° C., 9α,11β-dichloro-6α-fluoro-16α,17α,21,21-tetrahydroxypregna-1,4-diene-3,20-dione-16,17-acetonide-21,21-bis-methyl ether, m.p. 179°–181° C., 9α-chloro-6α-fluoro-11β,16α,17α,21,21-pentahydroxypregna-1,4-diene-3,20-dione-16,17-acetonide-21,21-bis-methyl ether, 6α,9α-difluoro-11β,17α,21,21-tetrahydroxy-16α-methylpregna-1,4-diene-3,20-dione-21,21-bis-methyl ether, 6α,9α-difluoro-11β,17α,21,21-tetrahydroxy-16α-methylpregna-1,4-diene-3,20-dione-17-caprylate-21,21-bis-methyl ether, 6α,9α-difluoro-11β,17α,21,21-tetrahydroxy-16α-methylpregna-1,4-diene-3,20-dione-17-benzoate-21,21-bis-methyl ether, 9α-fluoro-11β,17α,21,21-tetrahydroxy-16β-methylpregna-1,4-diene-3,20-dione-17-valerate-21,21-bis-methyl ether, m.p. 202°–204° C., 9α-fluoro-11β,17α,21,21-tetrahydroxy-16β-methylpregn-4-ene-3,20-dione-21,21-bis-methyl ether, 9α-fluoro-11β,16α,17α,21,21-pentahydroxypregna-1,4-diene-3,20-dione-16,17-acetonide-21,21-bis-methyl ether, m.p. 280°–282° C., 6α,9α-difluoro-11β,17α,21,21-tetrahydroxy-16α-methylpregna-1,4-diene-3,20-dione-17-acetate-21,21-bis-methyl ether, m.p. 226°–228° C., 11β,16α,17α,21,21-pentahydroxypregn-4-ene-3,20-dione-16,17-acetonide-21,21-bis-methyl ether, m.p. 250°–253° C., 11β,16α,17α,21,21-pentahydroxypregna-1,4-diene-3,20-dione-16,17-acetonide-21,21-bis-methyl ether, m.p. 154°–158° C., 6α-chloro-11β,16α,17α,21,21-pentahydroxypregn-4-ene-3,20-dione-16,17-acetonide-21,21-bis-methyl ether, 6α-fluoro-11β,16α,17α,21,21-pentahydroxypregna-1,4-diene-3,20-dione-16,17-acetonide-21,21-bis-ethyl ether, 6α,9α-difluoro-11β,16α,17α,21,21-pentahydroxypregn-4-ene-3,20-dione-16,17-acetonide-21,21-bis-ethyl ether, 6α-fluoro-11β,16α,17α,21,21-pentahydroxypregn-4-ene-3,20-dione-16,17-acetonide-21,21-bis-ethyl ether, 9α,11β-dichloro-6α-fluoro-16α,17α,21,21-tetrahydroxypregna-1,4-diene-3,20-dione-16,17-acetonide-21,21-bis-ethyl ether, 9α-chloro-6α-fluoro-11β,16α,17α,21,21-pentahydroxypregna-1,4-diene-3,20-dione-16,17-acetonide-21,21-bis-ethyl ether, 6α,9α-difluoro-11β,17α,21,21-tetrahydroxy-16α-methylpregna-1,4-diene-3,20-dione-21,21-bis-ethyl ether, 6α,9α-difluoro-11β,17α,21,21-tetrahydroxy-16α-methylpregna-1,4-diene-3,20-dione-17-caprylate-21,21-bis-ethyl ether, 6α,9α-difluoro-11β,17α,21,21-tetrahydroxy-16α-methylpregna-1,4-diene-3,20-dione-17-benzoate-21,21-bis-ethyl ether, 9α-fluoro-11β,17α,21,21-tetrahydroxy-16β-methylpregna-1,4-diene-3,20-dione-17-valerate-21,21-bis-ethyl ether, 9α-fluoro-11β,17α,21,21-tetrahydroxy-16β-methylpregn-4-ene-3,20-dione-21,21-bis-ethyl ether, 9α-fluoro-11β,16α,17α,21,21-pentahydroxypregna-1,4-diene-3,20-dione-16,17-acetonide-21,21-bis ethyl ether, 6α,9α-difluoro-11β,17α,21,21-tetrahydroxy-16α-methylpregna-1,4-diene-3,20-dione-17-acetate-21,21-bis-ethyl ether, 11β,16α,17α,21,21-pentahydroxypregn-4-ene-3,20-dione-16,17-acetonide-21,21-bis-ethyl ether, m.p. 224°–227° C., 11β,16α,17α,21,21-pentahydroxypregna-1,4-diene-3,20-dione-16,17-acetonide-21,21-bis-ethyl ether, 6α-chloro-11β,16α,17α,21,21-pentahydroxypregn-4-ene-3,20-dione-16,17-acetonide-21,21-bis-ethyl ether, 6α-fluoro-11β,16α,17α,21,21-pentahydroxypregna-1,4-diene-3,20-dione-16,17-acetonide-21,21-bis-n-propyl ether, 6α,9α-difluoro-11β,16α,17α,21,21-pentahydroxypregn-4-ene-3,20-dione-16,17-acetonide-21,21-bis-n-propyl ether, 6α-fluoro-11β,16α,17α,21,21-pentahydroxypregn-4-ene-3,20-dione-16,17-acetonide-21,21-bis-n-propyl ether, 9α,11β-dichloro-6α-fluoro-16α,17α,21,21-tetrahydroxypregna-1,4-diene-3,20-dione-16,17-acetonide-21,21-bis-n-propyl ether, 9α-chloro-6α-fluoro-11β,16α,17α,21,21-pentahydroxypregna-1,4-diene-3,20-dione-16,17-acetonide-21,21-bis-n-propyl ether, 6α,9α-difluoro-11β,17α,21,21-tetrahydroxy-16β-methylpregna-1,4-diene-3,20-dione-21,21-bis-n-propyl ether, m.p. 202°–204° C., 6α,9α-difluoro-11β,17α,21,21-tetrahydroxy-16α-methylpregna-1,4-diene-3,20-dione-17-caprylate-21,21-bis-n-propyl ether, 6α,9α-difluoro-11β,17α,21,21-tetrahydroxy-16α,-methylpregna-1,4-diene-3,20-dione-17-benzoate-21,21-bis-n-propyl ether, 9α-fluoro-11β,17α,21,21-tetrahydroxy-16β-methylpregna-1,4-diene-3,20-dione-17-valerate-21,21-bis-n-propyl ether, 9α-fluoro-11β,17α,21,21-tetrahydroxy-16β-methylpregn-4-ene-3,20-dione-21,21-bis-n-propyl ether, 9α-fluoro-11β,16α,17α,21,21-pentahydroxypregna-1,4-diene-3,20-dione-16,17-acetonide-21,21-bis-n-propyl ether, 6α,9α-difluoro-11β,17α,21,21-tetrahydroxy-16α-methylpregna-1,4-diene-3,20-dione-17-acetate-21,21-bis-n-propyl ether, 11β,16α,17α,21,21-pentahydroxypregn-4-ene-3,20-dione-16,17-acetonide-21,21-bis-n-propyl ether, 11β,16α,17α,21,21-pentahydroxypregna-1,4-diene-3,20-dione-16,17-acetonide-21,21-bis-n-propyl ether, 6α-chloro-11β,16α,17α,21,21-pentahydroxypregn-4-ene-3,20-dione-16,17-acetonide-21,21-bis-n-propyl ether, 6α-fluoro-11β,16α,17α,21,21-pentahydroxypregna-1,4-diene-3,20-dione-16,17-acetonide-21,21-bis-n-amyl ether, 6α-fluoro-11β,16α,17α,21,21-pentahydroxypregn-4-ene-3,20-dione-16,17-acetonide-21,21-bis-n-hexyl ether, 9α-chloro-6α-fluoro-11β,16α,17α,21,21-pentahydroxypregna-1,4-diene-3,20-dione-16,17-acetonide-21,21-bis-n-octyl ether, 9α-fluoro-11β,17α,21,21-tetrahydroxy-16β-methylpregna-1,4-diene-3,20-dione-17-valerate-21,21-bis-n-heptyl ether, 9α-fluoro-11β,16α,17α,21,21-pentahydroxypregna-1,4-diene-3,20-dione-16,17-acetonide-21,21-bis-n-butyl ether, 11β,16α,17α,21,21-pentahydroxypregn-4-ene-3,20-dione-16,17-acetonide-21,21-bis-n-octyl ether, 6α-fluoro-11β,16α,17α,21,21-pentahydroxypregna-1,4-diene-3,20-dione-16,17-acetonide-21-methyl-21-ethyl ether, 6α,9α-difluoro-11β,16α,17α, 21,21-pentahydroxypregn-4-ene-3,20-dione-16,17-acetonide-21-methyl-21-ethyl ether, 6α-fluoro-11β,16α,17α, 21,21-pentahydroxypregn-4-ene-3,20-dione-16,17-acetonide-21-methyl-21-ethyl ether, 9α,11β-dichloro-6α-fluoro-16α,17α,21,21-tetrahydroxypregna-1,4-diene-3,20-dione-16,17-acetonide-21-methyl-21-ethyl ether, 9α-chloro-6α-fluoro-11β,16α,17α,21,21-pentahydroxypregna-1,4-diene-3,20-dione-16,17-acetonide-21-methyl-21-ethyl ether, 6α,9α-difluoro-11β,17α,21,21-tetrahydroxy-16α-methylpregna-1,4-diene-3,20-dione-21-methyl-21-ethyl ether, 6α,9α-difluoro-11β,17α,21,21-tetrahydroxy-16α-methylpregna-1,4-diene-3,20-dione-17-caprylate-21-methyl-21-ethyl ether, 6α,9α-difluoro-11β,17α,21,21-tetrahydroxy-16α-methylpregna-1,4-diene-3,20-dione-17-benzoate-21-methyl-21-ethyl ether, 9α-fluoro-11β,17α,21,21-tetrahydroxy-16β-methylpregna-1,4-diene -3,20-dione-17-valerate-21-methyl-21-ethyl ether, 9α-fluoro-11β,17α,21,21-tetrahydroxy-16β-methylpregn-4-ene-3,20-dione-21-methyl-21ethyl ether, 9α-fluoro-11β,16α,17α,21,21-pentahydroxypregna-1,4-diene-3,20-dione-16,17-acetonide-21-methyl-21-ethyl ether, 6α,9α-difluoro-11β,17α,21,21-tetrahydroxy-16α-methylpregna-1,4-diene-3,20-dione-17acetate-21-methyl-21-ethyl ether, 11β,16α,17α,21,21-pentahydroxypregn-4-ene-3,20-dione-16,17-acetonide-21-methyl-21-ethyl ether, 11β,16α,17α,21,21-pentahydroxypregna-1,4-diene-3,20-dione-16,17-acetonide-21-methyl-21-ethyl ether, 6α-chloro-11β,16α,17α,21,21-pentahydroxypregn-4-ene-3,20-dione-16,17-acetonide-21-methyl-21-ethyl ether, 6α-fluoro-11β,16α,17α,21,21-pentahydroxypregna-1,4-diene-3,20-dione-16,17-acetonide-21-n-propyl ether, 60α,9α-difluoro-11β,16α,17α,21,21-pentahydroxypregn-4-ene-3,20-dione-16,17-acetonide-21-methyl-21-n-propyl ether, 6α-fluoro-11β,16α,17α,21,21-pentahydroxypregn-4-ene-3,20-dione-16,17-acetonide-21-methyl-21-n-propyl ether, 9α,11β-dichloro-6α-fluoro-16α,17α,21,21-tetrahydroxypregna-1,4-diene-3,20-dione-16,17-acetonide-21-methyl-21-n-propyl ether, 9α-chloro-6α-fluoro-11β,16α,17α,21,21-pentahydroxypregna-1,4-diene-3,20-dione-16,17-acetonide-21-methyl-21-n-propyl ether, 6α,9α-difluoro-11β,17α,21,21-tetrahydroxy-16α-methylpregna-1,4-diene-3,20-dione-21-methyl-21-n-propyl ether, m.p. 172°–175° C., 6α,9α-difluoro-11β,17α,21,21-tetrahydroxy-16α-methylpregna-1,4-diene-3,20-dione-17-caprylate-21-methyl-21-n-propyl ether, 6α,9α-difluoro-11β,17α,21,21-tetrahydroxy-16α-methylpregna-1,4-diene-3,20-dione-17-benzoate-21-methyl-21-n-propyl ether, 9α-fluoro-11β,17α,21,21-tetrahydroxy-16β-methylpregna-1,4-diene-3,20-dione-17-valerate-21-methyl-21-n-propyl ether, 9α-fluoro-11β,17α,21,21-tetrahydroxy-16β-methylpregn-4-ene-3,20-dione-21-methyl-21-n-propyl ether, 9α-fluoro-11β,16α,17α,21,21-pentahydroxypregna-1,4-diene-3,20-dione-16,17-acetonide-21-methyl-21-n-propyl ether, 6α,9α-difluoro-11β,17α,21,21-tetrahydroxy-16α-methylpregna-1,4-diene-3,20-dione-17-acetate-21-methyl-21-n-propyl ether, 11β,16α,17α,21,21-pentahydroxypregn-4-ene-3,20-dione-16,17-acetonide-21-methyl-21-n-propyl ether, 11β,16α,17α,21,21-pentahydroxypregna-1,4-diene-3,20-dione-16,17-acetonide-21-methyl-21-n-propyl ether, 6α-chloro-11β,16α,17α,21,21-pentahydroxypregn-4-ene-3,20-dione-16,17-acetonide-21-methyl-21-n-propyl ether, 6α-fluoro-11β,16α,17α,21,21-pentahydroxypregna-1,4-diene-3,20-dione-16,17-acetonide-21-ethyl-21n-propyl ether, 6α,9α-difluoro-11β,16α,17α,21,21-pentahydroxypregn-4-ene-3,20-dione-16,17-acetonide-21-ethyl-21-n-propyl ether, 6α-fluoro-11β,16α,17α,21,21-pentahydroxypregn-4-ene-3,20-dione-16,17-acetonide-21-n-propyl ether, 9α,11β-dichloro-6α-fluoro-16α,17α,21,21-tetrahydroxypregna-1,4-diene-3,20-dione-16,17-acetonide-21-ethyl-21-n-propyl ether, 9α-chloro-6α-fluoro-11β,16α,17α,21,21-pentahydroxypregna-1,4-diene-3,20-dione-16,17-acetonide-21-ethyl-21-n-propyl ether, 6α,9α-difluoro-11β,17α,21,21-tetrahydroxy-16αmethylpregna-1,4-diene-3,20-dione-21-ethyl-21-n-propyl ether, 6α,9α-difluoro-11β,17α,21,21-tetrahydroxy-16α-methylpregna-1,4-diene-3,20-dione-17-caprylate-21-ethyl-21-n-propyl ether, 6α,9α-difluoro-11β,17α,21,21-tetrahydroxy-16α-methylpregna-1,4-diene-3,20-dione-17-benzoate-21-ethyl21n-propyl ether, 9α-fluoro-11β,17α,21,21-tetrahydroxy-16β-methylpregna-1,4-diene-3,20-dione-17-valerate-21-ethyl-21n-propyl ether, 9α-fluoro-11β,17α,21,21-tetrahydroxy-16β-methylpregn-4-ene-3,20-dione-21-ethyl-21n-propyl ether, 9α-fluoro-11β,16α,17α,21,21-pentahydroxypregna-1,4-diene-3,20-dione-16,17-acetonide-21-ethyl-21-n-propyl ether, 6α,9α-difluoro-11β,17α,21,21-tetrahydroxy-16α-methylpregna-1,4-diene-3,20-dione-17-acetate-21-ethyl-21-n-propyl ether, 11β,16α,17α,21,21-pentahydroxypregn-4-ene-3,20-dione-16,17-acetonide-21-ethyl-21-n-propyl ether, 11β,16α,17α,21,21-pentahydroxypregna-1,4-diene-3,20-dione-16,17-acetonide-21-ethyl-21-n-propyl ether, 6α-chloro-11β,16α,17α,21,21-pentahydroxypregn-4-ene-3,20-dione-16,17-acetonide-21-ethyl-21-n-propyl ether, 6α-fluoro-11β,16α,17α,21,21-pentahydroxypregn-4-ene-3,20-dione-16,17-acetonide-21-methyl-21n-butyl ether, 6α,9α-difluoro-11β,17α,21,21-tetrahydroxy-6α-methylpregna-1,4-diene-3,20-dione-21-ethyl-21-n-butyl ether, 9α-fluoro-11β,16α,17α,21,21-pentahydroxypregna-1,4-diene-3,20-dione-16,17-acetonide-21-isopropyl-21-n-butyl ether, 6α-fluoro-11β,16α,17α,21,21-pentahydroxypregna-1,4-diene-3,20-dione-16,17-acetonide-21-n-hexyl-21-n-propyl ether, 6α,9α-difluoro-11β,16α,17α,21,21-pentahydroxypregn-4-ene-3,20-dione-16,17-acetonide-21-methyl-21n-octyl ether, 6α-fluoro-11β,16α,17α,21,21-pentahydroxypregn-4-ene-3,20-dione-16,17-acetonide-21-ethyl-21-n-hexyl ether, 9α,11β-dichloro-6α-fluoro-16α,17α,21,21-tetrahydroxypregna-1,4-diene-3,20-dione-16,17-acetonide-21-isopropyl-21-n-heptyl ether, 9α-chloro-6α-fluoro-11β,16;60 ,17α,21,21-pentahydroxypregna-1,4-diene-3,20-dione16,17-acetonide-21-methyl-21-n-hexyl ether, 6α,9α-difluoro-11β,17α, 21,21-tetrahydroxy-16α-methylpregna-1,4-diene-3,20-dione-21-ethyl-21-n-heptyl ether, 6α,9α-difluoro-11β,17α,21,21-tetrahydroxy-16α-methylpregna-1,4-diene-3,20-dione-17-caprylate-21-methyl-21-n-octyl ether, 6α,9α-difluoro-11β,17α,21,21-tetrahydroxy-16α-methylpregna-1,4-diene-3,20-dione-17-benzoate-21-methyl-21-n-octyl ether, 9α-fluoro-11β,17α,21,21-tetrahydroxy-16β-methylpregna-1,4-diene-3,20-dione-17-valerate-21-n-octyl-21-n-propyl ether, 9α-fluoro-11β,17α,21,21-tetrahydroxy-16β-methylpregn-4-ene-3,20-dione-21-n-heptyl ether, 9α-fluoro-11β,16α,17;60 ,21,21-pentahydroxypregna-1,4-diene-3,20-dione-16,17-acetonide-21-ethyl-21-n-octyl ether, 6α,9α-difluoro-11β,17α,21,21-tetrahydroxy-16α-methylpregna-1,4-diene-3,20-dione-17acetate-21-n-amyl-21-n-propyl ether, 11β,16α,17α,21,21-pentahydroxypregn-4-ene-3,20-dione-16,17-acetonide-21-methyl-21-n-octyl ether, 11β,16α,17α,21,21-pentahydroxypregna-1,4-diene-3,20-dione-16,17-acetonide-21-n-propyl-21-n-octyl ether, 6α,9α-difluoro-11β,16α,17α,21,21-pentahydroxypregn-4-ene-3,20-dione-16,17-acetonide-21-n-amyl-21n-hexyl ether, 9α,11β-dichloro-6α-fluoro-16α,17α,21,21-tetrahydroxypregna-1,4-diene-3,20-dione-16,17-acetonide-21-n-heptyl-21-n-hexyl ether, 6α,9α-difluoro-11β,17α,21,21-tetrahydroxy-16α-methylpregna-1,4-diene-3,20-dione-21-n-amyl-21-n-heptyl ether, 9α-fluoro-11β,17α,21,21-tetrahydroxy-16β-methylpregn-4-ene-3,20-dione-21-n-hexyl -n-octyl ether, 6α,9α-difluoro-11β,17α,21,21-tetrahydroxy-16α-methylpregna-1,4-diene-3,20-dione-17-acetate-21n-amyl-21-n-octyl ether, 21-azido-6α-fluoro-11β,16α,17α,21-tetrahydroxypregna-1,4-diene-3,20-dione-16,17-acetonide-21-methyl ether, 21-azido-6α,9α-difluoro-11β,16α,17α,21-tetrahydroxypregn-4-ene-3,20-dione-16,17-acetonide-21-methyl ether, 21-azido-6α-fluoro-11β,16α,17α,21-tetrahydroxypregna-1,4-diene-3,20-dione-16,17-acetonide-21-methyl ether, 21-azipo-9α,11β-dichloro-6α-fluoro-16α,17α,21-trihydroxypregna-1,4-diene-3,20-dione-16,17-acetonide-21-methyl ether, 21-azido-9α-chloro-6α-fluoro-11β,16α,17α,21-tetrahydroxypregna-1,4-diene-3,20-dione-16,17-acetonide-21-methyl ether, 21-azido-6α,9α-difluoro-11β,17α,21-trihydroxy-16α-methylpregna 1,4-diene-3,20-dione-21-methyl ether,
21-azido-6α,9α-difluoro-11β,17α,21-trihydroxy-16α-methylpregna-1,4-diene-3,20-dione-17-caprylate-21-methyl ether,
21-azido-6α,9α-difluoro-11β,17α,21-trihydroxy-16α-methylpregna-1,4-diene-3,20-dione-17-benzoate-21-methyl ether,
21-azido-9α-fluoro-11β,17α,21-trihydroxy-16β-methylpregna-1,4-diene-3,20-dione-17-valerate-21-methyl ether,
21-azido-9α-fluoro-11β,17α,21-trihydroxy-16β-methylpregn-4ene-3,20-dione-21-methyl ether,
21-azido-9α-fluoro-11β,16α,17α,21-tetrahydroxypregna-1,4-diene-3,20-dione-21-methyl ether,
21-azido-6α,9α-difluoro-11β,17α,21-trihydroxy-16α-methylpregna-1,4-diene-3,20-dione-17 -acetate-21-methyl ether, frothing 199°–204° C.; decomp. 235°–245° C.,
21-azido-11β,16α,17α,21-tetrahydroxypregn-4-ene-3,20-dione-16,17-acetonide-21-methyl ether,
21-azido-11β,16α,17α,21-tetrahydroxypregna-1,4-diene-3,20-dione-16,17-acetonide-21-methyl ether,
21-azido-6α-chloro-11β,16α,17α,21-tetrahydroxypregn-4-ene-3,20-dione-16,17-acetonide-21-methyl ether,
21-azido-6α-fluoro-11β,16α,17α,21-tetrahydroxypregna-1,4-diene-3,20-dione-16,17-acetonide-21-ethyl ether,
21-azido-6α,9α-difluoro-11β,16;60 ,17α,21-tetrahydroxypregn-4-ene-3,20-dione-16,17-acetonide-21-ethyl ether,
21-azido-6α-fluoro-11β,16α,17α,21-tetrahydroxypregna-1,4-diene-3,20-dione-16,17-acetonide-21-ethyl ether,
21-azido-9α,11β-dichloro-6α-fluoro-16α,17α,21-trihydroxypregna-1,4-diene-3,20-dione-16,17-acetonide-21-ethyl ether,
21-azido-9α-chloro-6α-fluoro-11β,16α,17α,21-tetrahydroxypregna-1,4-diene-3,20-dione-16,17-acetonide-21-ethyl ether,
21-azido-6α,9α-difluoro-11β,17α,21-trihydroxy-16α-methylpregna-1,4-diene-3,20-dione-21-ethyl ether,
21-azido-6α,9α-difluoro-11β,17α,21-trihydroxy-16α-methylpregna-1,4-diene-3,20-dione-17-caprylate-21-ethyl ether,
21-azido-6α,9α-difluoro-11β,17α,21-trihydroxy-16α-methylpregna-1,4-diene-3,20-dione-17-benzoate-21-ethyl ether,
21-azido-9α-fluoro-11β,17α,21-trihydroxy-16β-methylpregna-1,4-diene-3,20-dione-17-valerate-21-ethyl ether,
21-azido-9α-fluoro-11β,17α,21-trihydroxy-16β-methylpregn-4-ene-3,20-dione-21-ethyl ether,
21-azido-9α-fluoro-11β,16α,17α,21-tetrahydroxypregna-1,4-diene-3,20-dione-21-ethyl ether,
21-azido-6α,9α-difluoro-11β,17α,21-trihydroxy-16α-methylpregna-1,4-diene-3,20-dione-17-acetate-21-ethyl ether,
21-azido-11β,16α,17α,21-tetrahydroxypregn-4-ene-3,20-dione-16,17-acetonide-21-ethyl ether,
21-azido-11β,16α,17α,21-tetrahydroxypregna-1,4-diene-3,20-dione-16,17-acetonide-21-ethyl ether, 21-azido-6α,9α-difluoro-11β,16α,17α,21-tetrahydroxypregn-4-ene-3,20-dione-16,17-acetonide-21-n-propyl ether,
21-azido-11β,16α,17α,21-tetrahydroxypregna-1,4-diene- 3,20-dione-16,17-acetonide-21-n-propyl ether,
21-azido-6α-fluoro-11β,16α,17α,21-tetrahydroxypregna-1,4-diene-3,20-dione-16,17-acetonide-21-n-amyl ether,
21-azido-9α-chloro-6α-fluoro-11β,16α,17α,21-tetrahydroxypregna-1,4-diene-3,20-dione-16,17-acetonide-21-n-heptyl ether,
21-azido-6α,9α-difluoro-11β,17α,21-trihydroxy-16α-methylpregna-1,4-diene-3,20-dione-21-sec-butyl ether,
21-azido-9α-fluoro-11β,16α,17α,21-tetrahydroxypregna-1,4-diene-3,20-dione-21-n-hexyl ether,
21-azido-6α,9α-difluoro-11β,17α,21-trihydroxy-16α-methylpregna-1,4-diene-3,20-dione-17-acetate-21-n-octyl ether,
6α-fluoro-11β,16α,17α,21-tetrahydroxy-21-thiocyano-pregna-1,4-diene-3,20-dione-16,17-acetonide-21-methyl ether,
6α,9α-difluoro-11β,16α,17α,21-tetrahydroxy-21-thiocyanopregn-4-ene-3,20-dione-16,17-acetonide-21-methyl ether,
6α-fluoro-11β,16α,17α,21-tetrahydroxy-21-thiocyano-pregn-4-ene-3,20-dione-16,17-acetonide-21-methyl ether,
9α,11β-dichloro-6α-fluoro-16α,17α,21-trihydroxy-21-thiocyano-pregna-1,4-diene-3,20-dione-16,17-acetonide-21-methyl ether,
9α-chloro-6α-fluoro-11β,16α,17α,21-tetrahydroxy-21-thiocyano-pregna-1,4-diene-3,20-dione-16,17-acetonide-21-methyl ether,
6α,9α-difluoro-11β,17α,21-trihydroxy-16α-methyl-21-thiocyano-pregna-1,4-diene-3,20-dione-21-methyl ether,
6α,9α-difluoro-11β,17α,21-trihydroxy-16α-methyl-21-thiocyano-pregna-1,4-diene-3,20-dione-17-caprylate-21-methyl ether,
6α,9α-difluoro-11β,17α,21-trihydroxy-16α-methyl-21-thiocyano-pregna-1,4-diene-3,20-dione-17-benzoate-21-methyl ether,
9α-fluoro-11β,17α,21-trihydroxy-16β-methyl-21-thiocyano-pregna-1,4-diene-3,20-dione-17-valerate-21-methyl ether,
9α-fluoro-11β,17α,21-trihydroxy-16β-methyl-21-thiocyano-pregn-4-ene-3,20-dione-21-methyl ether,
9α-fluoro-11β,16α,17α,21-tetrahydroxy-21-thiocyano-pregna-1,4-diene-3,20-dione-16,17-acetonide-21-methyl ether,
6α,9α-difluoro-11β,17α,21-trihydroxy-21-thoicyano-pregna-1,4-diene-3,20-dione-17-acetate-21-methyl ether,
11β,16α,17α,21-tetrahydroxy-21-thiocyano-pregn-4-ene-3,20-dione-16,17-acetonide-21-methyl ether,
11β,16α,17α,21-tetrahydroxy-21-thiocyano-pregna-1,4-diene-3,20-dione-16,17-acetonide-21-methyl ether,
6α-chloro-11β,16α,17α,21-tetrahydroxy-1643,5-dien--methyl ether,
6α-fluoro-11β,16α,17α,21-tetrahydroxy-21-thiocyano-pregna-1,4-diene-3,20-dione-16,17-acetonide-21-ethyl ether, 6α,9α-difluoro-11β,16α,17α,21-tetrahydroxy-21-thiocyano-pregn-4-ene-3,20-dione-16,17-acetonide-21-ethyl ether, 6α-fluoro-11β,16α,17α,21-tetrahydroxy-21-thiocyano-pregn-4-ene-3,20-dione-16,17-acetonide-21-ethyl ether, 9α,11β-dichloro-6α-fluoro-16α,17α,21-trihydroxy-21-thiocyano-pregna-1,4-diene-3,20-dione-16,17-acetonide-21-ethyl ether, 9α-chloro-6α;1-fluoro-11β,16α,17α,21-tetrahydroxy-21-thiocyano-pregna-1,43,20-dione-16,17-acetonide-21-ethyl ether, 6α,9α-difluoro-11β,17α,21-trihydroxy-16α-methyl-21-thiocyano-pregna-1,4-diene-3,20-dione-21-ethyl ether, 6α,9α-difluoro-11β,17α,21-trihydroxy-16α-methyl-21-thiocyano-pregna-1,4-diene-3,20-dione-17-caprylate-21-ethyl ether, 6α,9α-difluoro-11β,17α,21-trihydroxy-16α-methyl-21-thiocyano-pregna-1,4-diene-3,20-dione-17-benzoate-21-ethyl ether, 9α-fluoro-11β,17α,21-trihydroxy-16β-methyl-21-thiocyano-pregna-1,4-diene-3,20-dione-17-valerate-21-ethyl ether, 9α-fluoro-11β,17α,21-trihydroxy-16β-methyl-21-thiocyano-pregn-4-ene-3,20-dione-21-ethyl ether, 9α-fluoro-11β,16α,17α,21-tetrahydroxy-21-thiocyano-pregna-1,4-diene-3,20-16,17-acetonide-21-ethyl ether, 6α,9α-difluoro-11β,17α,21-trihydroxy-21-thiocyano-pregna-1,4-diene-3,20-dione-17-acetate-21-ethyl ether, 11β,16α,17α,21-tetrahydroxy-21-thiocyano-pregn-4-ene-3,20-dione-16,17-acetonide-21-ethyl ether, 11β,16α,17α,21-tetrahydroxy-21-thiocyano-pregna-1,4-diene-3,20-dione-16,17-acetonide-21-ethyl ether 6α-chloro-11β,16α,17α,21-tetrahydroxy-21-thiocyano-pregn-4-ene-3,20-dione-16,17-acetonide-21-ethyl ether, 6α-fluoro-11β,16α,17α,21-tetrahydroxy-21-thiocyano-pregna-1,4-diene-3,20-dione-16,17-acetonide-21-sec-butyl ether, 6α-fluoro-11β,16α,17α,21-tetrahydroxy-21-thiocyano-pregn-4-ene-3,20-dione-16,17-acetonide-21-n-octyl ether, 9α-chloro-6α-fluoro-11β,16α,17α,21-tetrahydroxy-21-thiocyano-pregna-1,4-diene-3,20-dione-16,17-acetonide-21n-propyl ether, 6α,9α-difluoro-11β,17α,21-trihydroxy-16α-methyl-21-thiocyano-pregna-1,4-diene-3,20-dione-17-caprylate-21-n-octyl ether, 9α-fluoro-11α,17α,21-trihydroxy-16β-methyl-21-thiocyano-pregna-1,4-diene-3,20-dione-17-valerate-21-n-hexyl ether, 9α-fluoro-11β,17α,21-trihydroxy-16β-methyl-21-thiocyano-pregn-4-ene-3,20-dione-21-n-propyl ether, 11β,16α,17α,21-tetrahydroxy-21-thiocyano-pregn-4-ene-3,20-dione-16,17-acetonide-21-n-hexyl ether, 11β,16α,17α,21-tetrahydroxy-21-thiocyano-pregna-1,4-diene-3,20-dione-16,17-acetonide-21-n-amyl ether, 21-cyano-6α-fluoro-11β,16α,17α,21-tetrahydroxypregna-1,4-diene-3,20-dione-16,17-acetonide-21-methyl ether, 21-cyano-6α,9α-difluoro-11β,16α,17α,21-tetrahydroxypregn-4-ene-3,20-dione-16,17-acetonide-21-methyl ether, 21-cyano-6α-fluoro-11β,16α,17α,21-tetrahydroxypregn-4-ene-3,20-dione-16,17-acetonide-21-methyl ether, 21-cyano-9α,11β-dichloro-6α-fluoro-16α,17α,21-trihydroxy-pregna-1,4-diene-3,20-dione-16,17-acetonide-21-methyl ether, 21-cyano-9α-chloro-6α-fluoro-11β,16α,17α,21-tetrahydroxypregna-1,4-diene-3,20-dione-16,17-acetonide-21-methyl ether, 21-cyano-6α,9α-difluoro-11β,17α,21-trihydroxy-16α-methylpregna-1,4-diene-3,20-dione-21-methyl ether, 21-cyano6α,9α-difluoro-11β,17α,21-trihydroxy-16α-methylpregna-1,4-diene-3,20-dione-17-caprylate-21-methyl ether, 21-cyano-6α,9α-difluoro-11β,17α,21-trihydroxy-16α-methylpregna-1,4-diene-3,20-dione-17-benzoate-21-methyl ether, 21-cyano-9α-fluoro-11β,17α,21-trihydroxy-16β-methylpregna-1,4-diene-3,20-dione-17-valerate-21-methyl ether, 21-cyano9α-fluoro-11β,17α,21-trihydroxy-16β-methylpregn-4-ene-3,20-dione-21-methyl ether, 21-cyano-9α-fluoro-11β,16α,17α21-tetrahydroxypregna-1,4-diene-3,20-dione-16,17-acetonide-21-methyl ether, 21-cyano-6α,9α-difluoro-11β,17α,21-trihydroxypregna-1,4-diene-3,20-dione-17-acetate-21-methyl ether, 21-cyano-11β,16α,17α,21-tetrahydroxypregn-4-ene-3,20-dione-16,17-acetonide-21-methyl ether, 21-cyano-11β,16α,17α,21-tetrahydroxypregna-1,4-diene-3,20-dione-16,17-acetonide-21-methyl ether, 21-cyano-6α-chloro-11β,16α,17α,21-tetrahydroxypregn-4-ene-3,20-dione-16,17-acetonide-21-methyl ether, 21-cyano-6α-fluoro-11β, 16,60 ,17α,21-tetrahydroxypregna-1,4-diene-3,20-dione-16,17-acetonide-21-ethyl ether, 21-cyano-6α,9α-difluoro-11β,16α,17α,21-tetrahydroxypregn-4-ene-3,20-dione-16,17-acetonide-21-ethyl ether, 21-cyano-6α-fluoro-11β,16α,17α,21-tetrahydroxypregn-4-ene-3,20-dione-16,17-acetonide-21-ethyl ether, 21-cyano-9α,11β-dichloro-6α-fluoro-16α,17α,21-trihydroxypregna-1,4-diene-3,20-dione-16,17-acetonide-21-21-ethyl ether 21-cyano-9α-chloro-6α-fluoro-11β,16α,17α,21-tetrahydroxypregna-1,4-diene-3,20-dione-16,17-acetonide-21-ethyl ether, 21-cyano-6α,9α-difluoro-11β,17α,21-trihydroxy-16α-methylpregna-1,4-diene-3,20-dione-21-ethyl ether, 21-cyano-6α,9α-difluoro-11β,17α,21-trihydroxy-16α-methylpregna-1,4-diene-3,20-dione-17-caprylate-21-ethyl ether, 21-cyano-6α,9α-difluoro-11β,17α,21-trihydroxy-16α-methylpregna-1,4-diene-3,20-dione-17-benzoate-21-ethyl ether, 21-cyano-9α-fluoro-11β,17α,21-trihydroxy-16β-methylpregna-1,4-diene-3,20-dione-17-valerate-21-ethyl ether, 21-cyano-9α-fluoro-11β,17α,21-trihydroxy-16β-methylpregn-4-ene-3,20-dione-21-ethyl ether,
21-cyano-9α-fluoro-11β,16α,17α,21-tetrahydroxypregna-1,4-diene-3,20-dione-16,17-acetonide-21-ethyl ether,
21-cyano-6α,9α-difluoro-11β,17α,21-trihydroxypregna-1,4-diene-3,20-dione-17-acetate-21-ethyl ether,
21-cyano-11β,16α,17α,21-tetrahydroxypregn-4-ene-3,20-dione-16,17-acetonide-21-ethyl ether,
21-cyano-11β,16α,17α,21-tetrahydroxypregna-1,4-diene-3,20-dione-16,17-acetonide-21-ethyl ether,
21-cyano-6α-chloro-11β,16α,17α,21-tetrahydroxypregn-4-ene-3,20-dione-16,17-acetonide-21-ethyl ether,
21-cyano-6α,9α-difluoro-11β,16α,17α,21-tetrahydroxypregn-4-ene-3,20-dione-16,17-acetonide-21-n-octyl ether,
21-cyano-6α-fluoro-11β,16α,17α,21-tetrahydroxypregn-4-ene-3,20-dione-16,17-acetonide-21-n-propyl ether,
21-cyano-9α,11β-dichloro-6α-fluoro-16α,17α,21-trihydroxypregna-1,4-diene-3,20-dione-16,17-acetonide-21-n-butyl n-butyl ether,
21-cyano-6α,9α-difluoro-11β,17α,21-trihydroxy-16α-methylpregna-1,4-diene-3,20-dione-21-n-hexyl ether,
21-cyano-9α-fluoro-11β,16α,17α,21-tetrahydroxypregna-1,4-diene-3,20-dione-16,17-acetonide-21-n-heptyl ether, ether,
21-cyano-6α,9α-difluoro-11β,17α,21-trihydroxypregna-1,4-diene-3,20-dione-17-acetate-21-n-propyl ether,
21-cyano-11β,16α,17α21-tetrahydroxypregn-4-ene-3,20-dione-16,17-acetonide-21-n-amyl ether,
6α-fluoro-11β,16α,17α,21-tetrahydroxy-21-thiophenyl-pregna-1,4-diene-3,20-dione-16,17-acetonide-21-methyl ether,
6α,9α-difluoro-11β, 16α,17α,21-tetrahydroxy-21-thiophenyl-pregn-4-ene-3,20-dione-16,17-acetonide-21-methyl ether,
6α-fluoro-11β,16α,17α,21-tetrahydroxy-21-thiophenyl-pregn-4-ene-3,20-dione-16,17-acetonide-21-methyl ether,
9α,11β-dichloro-6α-fluoro-16α,17α,21-trihydroxy-21-thiophenyl-pregna-1,4-diene-3,20-dione-16,17-acetonide-21-methyl ether,
9α-chloro-6α-fluoro-11β,16α,17α,21-tetrahydroxy-21-thiophenyl-pregna-1,4-diene-3,20-dione-16,17-acetonide-21-methyl ether,
6α,9α-difluoro-11β,17α,21-trihydroxy-16α-methyl-21-thiophenyl-pregna-1,4-diene-3,20-dione-21-methyl ether,
6α,9α-difluoro-11β,17α,21-trihydroxy-16α-methyl-21-thiophenyl-pregna-1,4-diene-3,20-dione-17-caprylate-21-methyl ether,
6α,9α-difluoro-11β,17α,21-trihydroxy-16α-methyl-21-thiophenyl-pregna-1,4-diene-3,20-dione-17-benzoate-21-methyl ether,
9α-fluoro-11β,17α,21-trihydroxy-16β-methyl-21-thiophenylpregna-1,4-diene-3,20-dione-17-valerate-21-methyl ether,
9α-fluoro-11β,17α,21-trihydroxy-16β-methyl-21-thiophenyl-pregn-4-ene-3,20-dione-21-methyl ether,
9α-fluoro-11β,16α,17α,21-tetrahydroxy-21-thiophenylpregna-1,4-diene-3,20-dione-16,17-acetonide-21-methyl ether,
6α,9α-difluoro-11β,17α,21-trihydroxy-21-thiophenylpregna-1,4-diene-3,20-dione-17-acetate-21-methyl ether,
11β,16α,17α,21-tetrahydroxy-21-thiophenyl-pregn-4-ene-3,20-dione-16,17-acetonide-21-methyl ether,
11β,16α,17α,21-tetrahydroxy-21-thiophenyl-pregna-1,4-diene-3,20-dione-16,17-acetonide-21-methyl ether,
6α-chloro-11β,16α,17α,21-tetrahydroxy-21-thiophenylpregn-4-ene-3,20-dione-16,17-acetonide-21-methyl ether,
6α-fluoro-11β,16α,17α,21-tetrahydroxy-21-thiophenylpregna-1,4-diene-3,20-dione-16,17-acetonide-21-ethyl ether,
6α,9α-difluoro-11β,16α,17α,21-tetrahdyroxy-21-thiophenyl-pregn-4-ene-3,20-dione-16,17-acetonide-21-ethyl ether,
6α-fluoro-11β,16α,17α,21-tetrahydroxy-21-thiophenylpregn-4-ene-3,20-dione-16,17-acetonide-21-ethyl ether,
9α,11β-dichloro-6α-fluoro-16α,17α,21-trihydroxy-21-thiophenyl-pregna-1,4-diene-3,20-dione-16,17-acetonide-21-ethyl ether,
9α-chloro-6α-fluoro-11β,16α,17α,21-tetrahydroxy-21-thiophenyl-pregna-1,4-diene-3,20-dione-16,17-acetonide-21-ethyl ether,
6α,9α-difluoro-11β,17α,21-trihydroxy-16α-methyl-21-thiophenyl-pregna-1,4-diene-3,20-dione-21-ethyl ether,
6α,9α-difluoro-11β,17α,21-trihydroxy-16α-methyl-21-thiophenyl-pregna-1,4-diene-3,20-dione-17-caprylate-21-ethyl ether,
6α,9α-difluoro-11β,17α,21-trihydroxy-16α-methyl-21-thiophenyl-pregna-1,4-diene-3,20-dione-17-benzoate-21-ethyl ether,
9α-fluoro-11β,17α,21-trihydroxy-16β-methyl-21-thiophenyl-pregna-1,4-diene-3,20-dione-17-valerate-21-ethyl ether,
9α-fluoro-11β,17α,21-trihydroxy-16β-methyl-21-thiophenyl-pregn-4-ene-3,20-dione-21-ethyl ether,
9α-fluoro-11β,16α,17α,21-tetrahydroxy-21-thiophenylpregna-1,4-diene-3,20-dione-16,17-acetonide-21-ethyl ether,
6α,9α-difluoro-11β,17α,21-trihydroxy-21-thiophenylpregna-1,4-diene-3,20-dione-17-acetate-21-ethyl ether,
11β,16α,17α,21-tetrahydroxy-21-thiophenyl-pregn-4-ene-3,20-dione-16,17-acetonide-21-ethyl ether,
11β,16α,17α,21-tetrahydroxy-21-thiophenyl-pregna-1,4-diene-3,20-dione-16,17-acetonide-21-ethyl ether,
6α-chloro-11β,16α,17α,21-tetrahydroxy-21-thiophenylpregn-4-ene-3,20-dione-16,17-acetonide-21-ethyl ether,
6α-fluoro-11β,16α,17α,21-tetrahydroxy-21-thiophenylpregna-1,4-diene-3,20-dione-16,17-acetonide-21-n-propyl ether,
6α,9α-difluoro-11β,16α,17α,21-tetrahydroxy-21-thiophenyl-pregn-4-ene-3,20-dione-16,17-acetonide-21-n-amyl ether,
6α-fluoro-11β,16α,17α,21-tetrahydroxy-21-thiophenylpregn-4-ene-3,20-dione-16,17-acetonide-21-n-octyl ether,
9α,11β-dichloro-6α-fluoro-16α,17α,21-trihydroxy-21-thiophenyl-pregna-1,4-diene-3,20-dione-16,17-acetonide-21-isopropyl ether, 9α-chloro-6α-fluoro-11β,16α,17α,21-tetrahydroxy-21-thiophenyl-pregna-1,4-diene-3,20-dione-16,17-acetonide-21-n-hexyl ether, 9α-fluoro-11β,17α,21-trihydroxy-16β-methyl-21-thiophenyl-pregn-4-ene-3,20-dione-21-n-octyl ether, 6α,9α-difluoro-11β,17α,21-trihydroxy-21-thiophenylpregna-1,4-diene-3,20-dione-17-acetate-21-sec-butyl ether, 11β,16α,17α,21-tetrahydroxy-21-thiophenyl-pregna-1,4-diene-3,20-dione-16,17-acetonide-21-n-propyl ether, 6α-fluoro-11β,16α,17α,21-tetrahydroxy-21-thiomethyl-pregna-1,4-diene-3,20-dione-16,17-acetonide-21-methyl ether, 6α,9α-difluoro-11β,16α,17α,21-tetrahydroxy-21-thiomethyl-pregn-4-ene-3,20-dione-16,17-acetonide-21-methyl ether, 6α-fluoro-11β,16α,17α,21-tetrahydroxy-21-thiomethyl-pregn-4-ene-3,20-dione-16,17-acetonide-21-methyl ether, 9α,11β-dichloro-6α-fluoro-16α,17α,21-trihydroxy-21-thiomethyl-pregna-1,4-diene-3,20-dione-16,17-acetonide-21-methyl ether, 9α-chloro-6α-fluoro-11β,16α,17α,21-tetrahydroxy-21-thiomethyl-pregna-1,4-diene-3,20-dione-16,17-acetonide-21-methyl ether, 6α,9α-difluoro-11β,17α,21-trihydroxy-16α-methyl-21-thiomethyl-pregna-1,4-diene-3,20-dione-17-caprylate-21-methyl ether, 6α,9α-difluoro-11β,17α,21-trihydroxy-16α-methyl-21-thiomethyl-pregna-1,4-diene-3,20-dione-17-caprylate-21-methyl ether, 6α,9α-difluoro-11β,17α,21-trihydroxy-16α-methyl-21-thiomethyl-pregna-1,4-diene-3,20-dione-17-benzoate-21-methyl ether, 9α-fluoro-11β,17α,21-trihydroxy-16β-methyl-21-thiomethyl-pregna-1,4-diene-3,20-dione-17-valerate-21-methyl ether, 9α-fluoro-11β,17α,21-trihydroxy-16β-methyl-21-thiomethyl-pregn-4-ene-3,20-dione-21-methyl ether, 9α-fluoro-11β,16α,17α,21-tetrahydroxy-21-thiomethyl-pregna-1,4-diene-3,20-dione-16,17-acetonide-21-methyl ether, 6α,9α-difluoro-11β,17α,21-trihydroxy-21-thiomethyl-pregna-1,4-diene-3,20-dione-17-acetate-21-methyl ether, 11β,16α,17α,21-tetrahydroxy-21-thiomethyl-pregn-4-ene-3,20-dione-16,17-acetonide-21-methyl ether, 11β,16α,17α,21-tetrahydroxy-21-thiomethyl-pregna-1,4-diene-3,20-dione-16,17-acetonide-21-methyl ether, 6α-chloro-11β,16α,17α,21-tetrahydroxy-21-thiomethyl-pregn-4-ene-3,20-dione-16,17-acetonide-21-methyl ether, 9α-fluoro-11β,16α,17α,21-tetrahydroxy-21-thioethyl-pregna-1,4-diene-3,20-dione-16,17-acetonide-21-ethyl ether, 6α,9α-difluoro-11β,16α,17α,21-tetrahydroxy-21-thioethyl-pregn-4-ene-3,20-dione-16,17-acetonide-21-ethyl ether, 6α-fluoro-11β,16α,17α,21-tetrahydroxy-21-thioethyl-pregn-4-ene-3,20-dione-16,17-acetonide-21-ethyl ether, 9α,11β-dichloro-6α-fluoro-16α,17α,21-trihydroxy-21-thioethyl-pregna-1,4-diene-3,20-dione-16,17-acetonide-21-ethyl ether, 9α-chloro-6α-fluoro-11β,16α,17α,21-tetrahydroxy-21-thioethyl-pregna-1,4-diene-3,20-dione-16,17-acetonide-21-ethyl ether, 6α,9α-difluoro-11β,17α,21-trihydroxy-16α-methyl-21-thioethyl-pregna-1,4-diene-3,20-dione-21-ethyl ether, 6α,9α-difluoro-11β,17α,21-trihydroxy-16α-methyl-21-thioethyl-pregna-1,4-diene-3,20-dione-17-caprylate-21-ethyl ether, 6α,9α-difluoro-11β,17α,21-trihydroxy-16α-methyl-21-thioethyl-pregna-1,4-diene-3,20-dione-17-benzoate-21-ethyl ether, 9α-fluoro-11β,17α,21-trihydroxy-16β-methyl-21-thioethyl-pregna-1,4-diene-3,20-dione-17-valerate-21-ethyl ether, 9α-fluoro-11β,17α,21-trihydroxy-16β-methyl-21-thioethyl-pregn-4-ene-3,20-dione-21-ethyl ether, 9α-fluoro-11β,16α,17α,21-tetrahydroxy-21-thioethyl-pregna-1,4-diene-3,20-dione-16,17-acetonide-21-ethyl ether, 6α,9α-difluoro-11β,17α,21-trihydroxy-21-thioethyl-pregna-1,4-diene-3,20-dione-17-acetate-21-ethyl ether, 11β,16α,17α,21-tetrahydroxy-21-thioethyl-pregn-4-ene-3,20-dione-16,17-acetonide-21-ethyl ether, 11β,16α,17α,21-tetrahydroxy-21-thioethyl-pregna-1,4-diene-3,20-dione-16,17-acetonide-21-ethyl ether, 6α-chloro-11β,16α,17α,21-tetrahydroxy-21-thioethyl-pregn-4-ene-3,20-dione-16,17-acetonide-21-ethyl ether, 6α-fluoro-11β,16α,17α,21-tetrahydroxy-21-thio-n-propyl-pregna-1,4-diene-3,20-dione-16,17-acetonide-21-n-propyl ether, 6α-fluoro-11β,16α,17α,21-tetrahydroxy-21-thio-n-propyl-pregn-4-ene-3,20-dione-16,17-acetonide-21-n-propyl ether, 9α-fluoro-11β,17α,21-trihydroxy-16β-methyl-21-thio-n-propyl-pregna-1,4-diene-3,20-dione-17-valerate-21-n-propyl ether, 11β,16α,17α,21-tetrahydroxy-21-thio-n-propyl-pregna-1,4-diene-3,20-dione-16,17-acetonide-21-n-propyl ether, 6α-fluoro-11β,16α,17α,21-tetrahydroxy-21-thio-n-octyl-pregna-1,4-diene-3,20-dione-16,17-acetonide-21-n-octyl ether, 6α-fluoro-11β,16α,17α,21-tetrahydroxy-21-thio-sec-butyl-pregn-4-ene-3,20-dione-16,17-acetonide-21-sec-butyl ether, 9α-chloro-6α-fluoro-11β,16α,17α,21-tetrahydroxy-21-thio-n-heptyl-pregna-1,4-diene-3,20-dione-16,17-acetonide-21-n-heptyl ether, 9α-fluoro-11β,16α,17α,21-tetrahydroxy-21-thio-n-hexyl-pregna-1,4-diene-3,20-dione-16,17-acetonide-21-n-hexyl ether, 11β,16α,17α,21-tetrahydroxy-21-thio-n-amyl-pregna-1,4-diene-3,20-dione-16,17-acetonide-21-n-amyl ether, 6α-fluoro-11β,16α,17α,21-tetrahydroxy-21-thioethyl-pregna-1,4-diene-3,20-dione-16,17-acetonide-21-methyl ether, 6α,9α-difluoro-11β,16α,17α,21-tetrahydroxy-21-thioethyl-pregn-4-ene-3,20-dione-16,17-aceotnide-21-methyl ether, 6α-fluoro-11β,16α,17α,21-tetrahydroxy-21-thioethyl-pregn-4-ene-3,20-dione-16,17-acetonide-21-methyl ether, 9α,11β-dichloro-6α-fluoro-16α,17α,21-trihydroxy-21-thioethyl-pregna-1,4-diene-3,20-dione-16,17-acetonide-21-methyl ether, 9α-chloro-6α-fluoro-11β,16α,17α,21-tetrahdyroxy-21-thioethyl-pregna-1,4-diene-3,20-dione-16,17-acetonide-21-methyl ether, 6α,9α-difluoro-11β,17α,21-trihydroxy-16α-methyl-21-thioethyl-pregna-1,4-diene-3,20-dione-21-methyl ether, 6α,9α-difluoro-11β,17α,21-trihydroxy-16α-methyl-21-thioethyl-pregna-1,4-diene-3,20-dione-17-caprylate-21-methyl ether, 6α,9α-difluoro-11β,17α,21-trihydroxy-16α-methyl-21-thioethyl-pregna-1,4-diene-3,20-dione-17-benzoate-21-methyl ether, 9α-fluoro-11β,17α,21-trihydroxy-16β-methyl-21-thioethyl-pregna-1,4-diene-3,20-dione-17-acetate-21-methyl ether, 9α-fluoro-11β,17α,21-trihydroxy-16β-methyl-21-thioethyl-pregn-4-ene-3,20-dione-21-methyl ether, 9α-fluoro-11β,16α,17α,21-tetrahydroxy-21-thioethyl-pregna-1,4-diene-3,20-dione-16,17-acetonide-21-methyl ether, 6α,9α-difluoro-11β,17α,21-trihydroxy-21-thioethyl-pregna-1,4-diene-3,20-dione-17-acetate-21-methyl ether, 11β,16α,17α,21-tetrahydroxy-21-thioethyl-pregn-4-ene-3,20-dione-16,17-acetonide-21-methyl ether, 11β,16α,17α,21-tetrahydroxy-21-thioethyl-pregna-1,4-diene-3,20-dione-16,17-acetonide-21-methyl ether, 6α-chloro-11β,16α,17α,21-tetrahydroxy-21-thioethyl-pregn-4-ene-3,20-dione-16,17-acetonide-21-methyl ether, 6α-fluoro-11β,16α,17α,21-tetrahydroxy-21-thio-n-propylpregna-1,4-diene-3,20-dione-16,17-acetonide-21-methyl ether, 6α,9α-difluoro-11β,16α,17α,21-tetrahydroxy-21-thio-n-propyl-pregn-4-ene-3,20-dione-16,17-acetonide-21-methyl ether, 6α-fluoro-11β,16α,17α,21-tetrahydroxy-21-thio-n-propyl-pregn-4-ene-3,20-dione-16,17-acetonide-21-methyl ether, 9α,11β-dichloro-6α-fluoro-16α,17α,21-trihydroxy-21-thio-n-propyl-pregna-1,4-diene-3,20-dione-16,17-acetonide-21-methyl ether, 9α-chloro-6α-fluoro-11β,16α,17α,21-tetrahydroxy-21-thio-n-propyl-pregna-1,4-diene-3,20-dione-16,17-acetonide-21-methyl ether, 6α,9α-difluoro-11β,17α,21-trihydroxy-16α-methyl-21-thio-n-propyl-pregna-1,4-diene-3,20-dione-21-methyl ether, 6α,9α-difluoro-11β,17α,21-trihydroxy-16α-methyl-21-thio-n-propyl-pregna-1,4-diene-3,20-dione-17-caprylate-21-methyl ether, 6α,9α-difluoro-11β,17α,21-trihydroxy-16α-methyl-21-thio-n-propyl-pregna-1,4-diene-3,20-dione-17-benzoate-21-methyl ether, 9α-fluoro-11β,17α,21-trihydroxy-16β-methyl-21-thio-n-propyl-pregna-1,4-diene-3,20-dione-17-acetate-21-methyl ether, 9α-fluoro-11β,17α,21-trihydroxy-16β-methyl-21-thio-n-propyl-pregn-4-ene-3,20-dione-21-methyl ether, 9α-fluoro-11β,16α,17α,21-tetrahydroxy-21-thio-n-propyl-pregna-1,4-diene-3,20-dione-16,17-acetonide-21-methyl ether, 6α,9α-difluoro-11β,17α,21-trihydroxy-21-thio-n-propyl-pregna-1,4-diene-3,20-dione-17-acetate-21-methyl ether, 11β,16α,17α,21-tetrahydroxy-21-thio-n-propyl-pregn-4-ene-3,20-dione-16,17-acetonide-21-methyl ether, 11β,16α,17α,21-tetrahydroxy-21-thio-n-propyl-pregna-1,4-diene-3,20-dione-16,17-acetonide-21-methyl ether, 6α-chloro-11β,16α,17α,21-tetrahydroxy-21-thio-n-propyl-pregn-4-ene-3,20-dione-16,17-acetonide-21-methyl ether, 6α,9α-difluoro-11β,16α,17α,21-tetrahydroxy-21-thio-n-propyl-pregn-4-ene-3,20-dione-16,17-acetonide-21-ethyl ether, 6α-fluoro-11β,16α,17α,21-tetrahydroxy-21-thio-n-heptyl-pregn-4-ene-3,20-dione-16,17-acetonide-21-21-n-propyl ether, 9α-chloro-6α-fluoro-11β,16α,17α,21-tetrahydroxy-21-thio-n-propyl-pregna-1,4-diene-3,20-dione-16,17-acetonide-21-ethyl ether 6α,9α-difluoro-11β,17α,21-trihydroxy-16α-methyl-21-thio-n-heptyl-pregna-1,4-diene-3,20-dione-17-benzoate-21-isopropyl ether, 9α-fluoro-11β,17α,21-trihydroxy-16β-methyl-21-thio-n-hexyl-pregna-1,4-diene-3,20-dione-17-acetate-21-ethyl ether, 9α-fluoro-11β,16α,17α,21-tetrahydroxy-21-thio-n-propyl-pregna-1,4-diene-3,20-dione-16,17-acetonide-21-ethyl ether, 11β,16α,17α,21-tetrahydroxy-21-thio-n-octyl-pregn-4-ene-3,20-dione-16,17-acetonide-21-methyl ether.

21-chloro-11β,17α,21-trihydroxy-16α-methylpregna-1,4-diene-3,20-dione-17-valerate-21-methyl ether, 21-chloro-11β,17α,21-trihydroxy-16α-methylpregna-1,4-diene-3,20-dione-17-valerate-21-ethyl ether, 21-chloro-11β,17α,21-trihydroxy-16α-methylpregna-1,4-diene-3,20-dione-17-valerate-21-n-propyl ether, 11β,17α,21,21-tetrahydroxy-16α-methylpregna-1,4-diene-3,20-dione-17-valerate-21,21-bis-methyl ether, 11β,17α,21,21-tetrahydroxy-16α-methylpregna-1,4-diene-3,20-dione-17-valerate-21,21-bis-ethyl ether, 11β,17α,21,21-tetrahydroxy-16α-methylpregna-1,4-diene-3,20-dione-17-valerate-21,21-bis-n-propyl ether, 11β,17α,21,21-tetrahydroxy-16α-methylpregna-1,4-diene-3,20-dione-17-valerate-21-methyl-21-ethyl ether, 11β,17α,21,21-tetrahydroxy-16α-methylpregna-1,4-diene-3,20-dione-17-valerate-21-methyl-21-n-propyl ether, 21-azido-11β,17α,21-trihydroxy-16α-methylpregna-1,4-diene-3,20-dione-17-valerate-21-methyl ether, 11β,17α,21-trihydroxy-16α-methyl-21-thiocyanopregna-1,4-diene-3-20-dione-17-valerate -21-methyl ether, 21-cyano-11β,17α,21-trihydroxy-16α-methylpregna-1,4-diene-3,20-dione-17-valerate-21-methyl ether, 11β,17α,21-trihydroxy-16α-methyl-21-thiophenyl-pregna-1,4-diene-3,20-dione-17-valerate-21-methyl ether, 11β,17α,21-trihydroxy-16α-methyl-21-thiophenyl-pregna-1,4-diene-3,20-dione-17-valerate-21-ethyl ether, 11β,17α,21-trihydroxy-16α-methyl-21-thiomethyl-pregna-1,4-diene-3,20-dione-17-valerate-21-methyl ether,

EXAMPLE 13

In similar manner to procedures a) and b) of Example 11, using reactants as dictated by the particular 3-alkoxy-3,5-dien-21-acetal or 3-oxo-5- en-21-acetal desired, the following compounds are prepared:

6α-fluoro-3,11β,16α,17α,21,21-hexahydroxypregna-1,3,5-trien-20-one-16,17-acetonide-3,21,21-tris-methyl ether, 6α,9α-difluoro-3,11β,16α,17α,21,21-hexahydroxy-pregna-3,5 -dien-dien-20-one-16,17-acetonide-3,21,21-tris-methyl ether, 6α-fluoro-3,11β,16α,17α,21,21-hexahydroxypregna-3,5-dien-20-one-16,17-acetonide-3,21,21-tris-methyl ether, 9α,11β-dichloro-6α-fluoro-3,16α,17α,21,21-pentahydroxy-pregna-1,3,5 -trien-20-one-16,17-acetonide-3,21,21-tris-methyl ether, 9α-chloro-6α-fluoro-3,11β,16α,17α,21-21-hexahydroxypregna-1,3,5-trien-20-one-16,17-acetonide-3,21,21-tris-methyl ether, 6α,9α-difluoro-3,11β,17α,21,21-pentahydroxy-16-methylpregna-1,3,5-trien-20-one-3,21,21-tris-methyl ether, 6α,9α-difluoro-3,11β,17α,21,21-pentahydroxy-16-methylpregna-1,3,5-trien-20-one-17-caprylate-3,21,21-tris-methyl ether, 6α,9α-difluoro-3,11β,17α,21,21-pentahydroxy-16-methylpregna-1,3,5-trien-20-one-17-benzoate-3,21,21-tris-methyl ether, 9α-fluoro-3,11β,17α,21,21-pentahydroxy-16 -methylpregna-3,5 - dien-20-one-3,21,21-tris-methyl ether, 6α,9α-difluoro-3,11β,17α,21,21-pentahydroxy-16-methylpregna-1,3,5-trien-20-one-17-acetate-3,21,21-tris-methyl ether, 3,11β,16α,17α,21,21-hexahydroxypregna-3,5-dien-20one-16,17-acetonide-3,21,21-tris-methyl ether, 6α-chloro-3,11β,16α,17α,21,21-hexahydroxypren-ga-3,5-dien-20-one-16,17-acetonide-3,21,21-tris-methyl ether, 6α-fluoro-3,11β,16α,17α,21,21-hexahydroxypregna-1,3,5-trien-20-one-16,17-acetonide-3,21,21-tris-ethyl ether, 6α,9α-difluoro-3,11β,16α,17α,21,21-hexahydroxy-pregna-3,5-dien-20-one-16,17-acetonide-3,21,21-tris-ethyl ether, 6α-fluoro-3,11β,16α,17α,21,21-hexahydroxypregna-3,5-dien-20-one-16,17-acetonide-3,21,21-tris-ethyl ether, 9α,11β-dichloro-6α-fluoro-3.16α,17α,21,21-pentahydroxypregna-1,3,5-trien-20-one-16,17-acetonide-3,21,21-tris-ethyl ether, 9α-chloro-6α-fluoro-3,11β,16α,17α,21,21-hexahydroxypregna-1,3,5-trien-20-one-16,17-acetonide-3,21,21-tris-ethyl ether.

6α,9α-difluoro-3,11β,17α,21,21-pentahydroxy-16α-methylpregna-1,3,5-trien-20-one-3,21,21-tris-ethyl ether, 6α,9α-difluoro-3,11β,17α,21,21-pentahydroxy-16α-methylpregna-1,3,5-trien-20-one-17-caprylate-3,21,21-tris-ethyl ether, 6α,9α-difluoro-3,11β,17α,21,21-pentahydroxy-16α-methylpegna-1,3,5-trien-20-one-17-benzoate-3,21,21-tris-ethyl ether, 9α-fluoro-3,11β,17α,21,21-pentahydroxy-16β-methylpregna-3,5-dien-20-one-3,21,21-tris-ethyl ether, 6α,9α-difluoro-3,11β,17α,21,21-pentahydroxy-16α-methylpregna-1,3,5-trien-20-one-17-acetate-3,21,21-tris-ethyl ether, 3,11β,16α,17α,21,21-hexahydroxyprena-3,5-dien-20-one-16,17-acetonide-3,21,21-tris-ethyl ether, 3β,11β,16α,17α,21,21-hexahydroxypregna-1,3,5-trien--20-one-16,17-acetonide-3,21,21-tris-ethyl ether, 6α-chloro-3,11β,16α,17α,21,21-hexahydroxypregna-3,5-dien-20-one-16,17-acetonide-3,21,21-tris-ethyl ether, 60α-fluoro-3,11β,16α,17α,21,21-hexahydroxypregna-1,3,5-trien-20-one-16,17-acetonide-3,21,21-tris-isopropyl ether, 6α,9α-difluoro-3,11β,16α,17α,21,21-hexahydroxy-pregna-3,5-dien-20-one-16,17-acetonide-3,21,21-tris-n-propyl ether, 60α6α-fluoro -3,11β,16α,17α,21,21-hexahydroxypregna-3,5-dien-20-one-16,17-acetonide-3,21,21-tris-n-propyl ether, 9α,11β-dichloro-6α-fluoro-3,16α,17α,21,21-pentahydroxypregna-1,3,5-trien-20-one-16,17-acetonide-3,21,21-tris-n-propyl ether, 9α-chloro-6α-fluoro-3,11β,16α,17α,21,21-hexahydroxypregna-1,3,5-trien-20-one-16,17-acetonide-3,21,21-tris-n-propyl ether, 6α,9α-difluoro-3,11β,17α,21,21-pentahydroxy-16α-methylpregna-1,3,5-trien-20-one-3,21,21-tris-n-propyl ether, 6α,9α-difluoro-3,11β,17α,21,21-pentahydroxy-16α-mthylpregna-1,3,5-trien-20-one-17-caprylate-3,21,21-tris-n-propyl ether, 6α,9α-difluoro-3,11β,17α,21,21-pentahydroxy-16α-methylpregna-1,3,5-trien-20-one-17-benzoate-3,21,21-tris-n-propyl ether, 9α-fluoro-3,11β,17α,21,21-pentahydroxy-16β-methylpregna-3,5-dien-20-one-3,21,21-tris-n-propyl ether, 6α,9α-difluoro-3,11β,17α,21,21-pentahydroxy-16α-methylpregna-1,3,5-trien-20-one-17-acetate-3,21,21-tris-n-propyl ether, 3,11β,16α,17α,21,21-hexahydroxypregna-3,5-dien-20-one-16,17-acetonide-3,21,21-tris-n-propyl ether, 6α-chloro-3,11β,16α,17α,21,21-hexahydroxypregna-3,5-dien-20-one-16,17-acetonide-3-21,21-tris-n-propyl ether, 6α-fluoro-3,11β,16α,17α,21,21-hexahydroxypregna-1,3,5-trien-20-one-16,17-acetonide-3,21,21-tris-n-butyl ether, 6α,9α-difluoro-3,11β,16α,17α,21,21-hexahydroxy-pregna-3,5-dien-20-one-16,17-acetonide-3,21,21-tris-n-butyl ether, 6α-fluoro-3,11β,16α,17α,21,21-hexahydroxypregna-3,5-dien-20-one-16,17-acetonide-3,21,21-tris-n-butyl ether, 9α,11β-dichloro-6α-fluoro-3,16α,17α,21,21-pentahydroxypregna-1,3,5-trien-20-one-16,17-acetonide-3,21,21-tris-n-butyl ether, 9α-chloro-6α-fluoro-3,11β,16α,17α,21,21-hexahydroxypregna-1,3,5-trien-20-one-16,17-acetonide-3,21,21-tris-n-butyl ether, 6α,9α-difluoro-3,11β,17α,21,21-pentahydroxy-16α-methylpregna-1,3,5-trien-20-one-3,21,21-tris-n-butyl ether,
6α,9α-difluoro-3,11β,17α,21,21-pentahydroxy-16α-methylpregna-1,3,5-trien-20-one-17-caprylate-3,21,21-tris-n-butyl ether,
6α,9α-difluoro-3,11β,17α,21,21-pentahydroxy-16α-methylpregna-1,3,5-trien-20-one-17-benzoate-3,21,21-tris-n-butyl ether,
9α-fluoro-3,11β,17α,21,21-pentahydroxy-16β-methylpregna-3,5-dien-20-one-3,21,21-tris-n-butyl ether,
6α,9α-difluoro-3,11β,17α,21,21-pentahydroxy-16α-methylpregna-1,3,5-trien-20-one-17-acetate-3,21,21-tris-n-butyl ether,
3β,11β,16α,17α,21,21-hexahydroxypregna-3,5-dien-20-one-16,17-acetonide-3,21,21-tris-n-butyl ether,
6α-fluoro-11β,16α,17α,21,21-pentahydroxypregna-1,5-diene-3,20-dione-16,17-acetonide-21,21-bis-methyl ether,
6α,9α-difluoro-11β,16α,17α,21,21-pentahydroxypregn-5-ene-3,20-dione-16,17-acetonide-21,21-bis-methyl ether,
6α-fluoro-11β,16α,17α,21,21-pentahydroxypregn-5-ene-3,20-dione-16,17-acetonide-21,21-bis-methyl ether,
9α,11β-dichloro-6α-fluoro-16α,17α,21,21-tetrahydroxypregna-1,5-diene-3,20-dione-16,17-acetonide-21,21-bis-methyl ether,
9α-chloro-6α-fluoro-11β,16α,17α,21,21-pentahydroxypregna-1,5-diene-3,20-dione-16,17-acetonide-21,21-bis-methyl ether, 6α,9α-difluoro-11β,17α,21,21-tetrahydroxy-16α-methylpregna-1,5-diene-3,20-dione-21,21-bis-methyl ether,
6α,9α-difluoro-11β,17α,21,21-tetrahydroxy-16α-methylpregna-1,5-diene-3,20-dione-17-caprylate-21,21-bis-methyl ether,
6α,9α-difluoro-11β,17α,21,21-tetrahydroxy-16α-methylpregna-1,5-diene-3,20-dione-17-benzoate-21,21-bis-methyl ether,
9α-fluoro-11β,17α,21,21-tetrahydroxy-16β-methylpregna-5-ene-3,20-dione-21,21-bis-methyl ether,
6α,9α-difluoro-11β,17α,21,21-tetrahydroxy-16α-methylpregna-1,5-diene-3,20-dione-17-acetate-21,21-bis-methyl ether,
11β,16α,17α,21,21-pentahydroxypregn-5-ene-3,20-dione-16,17-acetonide-21,21-bis-methyl ether,
6α-chloro-11β,16α,17α,21,21-pentahydroxypregna-1,5-diene-3,20-dione-16,17-acetonide-21,21-bis-methyl ether, 6α-fluoro-11β,16α,17α,21,21-pentahydroxypregna-1,5-diene-3,20-dione-16,17-acetonide-21,21-bis-ethyl ether,
6α,9α-difluoro-11β,16α,17α,21,21-pentahydroxypregn-5-ene-3,20-dione-16,17-acetonide-21,21-bis-ethyl ether, 6α-fluoro-11β,16α,17α,21,21-pentahydroxypregn-5-ene-3,20-dione-16,17-acetonide-21,21-bis-ethyl ether,
9α,11β-dichloro-6α-fluoro-16α,17α,21,21-tetrahydroxypregna-1,5-diene-3,20-dione-16,17-acetonide-21,21-bis-ethyl ether,
9α-chloro-6α-fluoro-11β,16α,17α,21,21-pentahydroxypregna-1,5-diene-3,20-dione-16,17-acetonide-21,21-bis-ethyl ether,
6α,9α-difluoro-11β,17α,21,21-tetrahydroxy-16α-methylpregna-1,5-diene-3,20-dione-21,21-bis-ethyl ether,
6α,9α-difluoro-11β,17α,21,21-tetrahydroxy-16α-methylpregna-1,5-diene-3,20-dione-17-caprylate-21,21-bis-ethyl ether,
6α,9α-difluoro-11β,17α,21,21-tetrahydroxy-16α-methylpregna-1,5-diene-3,20-dione-17-benzoate-21,21-bis-ethyl ether,
9α-fluoro-11β,17α,21,21-tetrahydroxy-16β-methylpregna-5-ene-3,20-dione-21,21-bis-ethyl ether,
6α,9α-difluoro-11β,17α,21,21-tetrahydroxy-16α-methylpregna-1,5-diene-3,20-dione-17-acetate-21,21-bis-ethyl ether,
11β,16α,17α,21,21-pentahydroxypregn-5-ene-3,20-dione-16,17-acetonide-21,21-bis-ethyl ether, 6α-chloro-11β,16α,17α,21,21-pentahydroxypregn-5-ene-3,20-dione-16,17-acetonide-21,21-bis-ethyl ether,
6α-fluoro-11β,16α,17α,21,21-pentahydroxypregna-1,5-diene-3,20-dione-16,17-acetonide-21,21-bis-n-propyl ether,
6α,9α-difluoro-11β,16α,17α,21,21-pentahydroxypregn-5-ene-3,20-dione-16,17-acetonide-21,21-bis-isopropyl ether,
6α-fluoro-11β,16α,17α,21,21-pentahydroxypregn-5-ene-3,20-dione-16,17-acetonide-21,21-bis-n-propyl ether, 9α,11β-dichloro-6α-fluoro-16α,17α,21,21-tetrahydroxypregna-1,5-diene-3,20-dione-16,17-acetonide-21,21-bis-n-propyl ether,
9α-chloro-6α-fluoro-11β,16α,17α,21,21-pentahydroxypregna-1,5-diene-3,20-dione-16,17-acetonide-21,21-bis-n-propyl ether,
6α,9α-difluoro-11β,17α,21,21-tetrahydroxy-16α-methylpregna-1,5-diene-3,20-dione-21,21-bis-isopropyl ether,
6α,9α-difluoro-11β,17α,21,21-tetrahydroxy-16α-methylpregna-1,5-diene-3,20-dione-17-caprylate-21,21-bis-isopropyl ether,
6α,9α-difluoro-11β,17α,21,21-tetrahydroxy-16α-methylpregna-1,5-diene-3,20-dione-17-benzoate-21,21-bis-isopropyl ether,
9α-fluoro-11β,17α,21,21-tetrahydroxy-16β-methylpregn-5(6)-ene-3,20-dione-21,21-bis-isopropyl ether, 6α,9α-difluoro-11β,17α,21,21-tetrahydroxy-16α-methylpregna-1,5-diene-3,20-dione-17-acetate-21,21-bis-n-propyl ether,
11β,16α,17α,21,21-pentahydroxypregn-5-ene-3,20-dione-16,17-acetonide-21,21-bis-n-propyl ether,
6α-chloro-11β,16α,17α,21,21-pentahydroxypregn-5-ene-3,20-dione-16,17-acetonide-21,21-bis-n-propyl ether, 6α-fluoro-11β,16α,17α,21,21-pentahydroxypregna-1,5-diene-3,20-dione-16,17-acetonide-21,21-bis-n-butyl ether,
6α,9α-difluoro-11β,16α,17α,21,21-pentahydroxypregn-5-ene-3,20-dione-16,17-acetonide-21,21-bis-n-butyl ether,
6α-fluoro-11β,16α,17α,21,21-pentahydroxypregn-5-ene-3,20-dione-16,17-acetonide-21,21-bis-n-butyl ether,
9α,11β-dichloro-6α-fluoro-16α,17α,21,21-tetrahydroxypregna-1,5-diene-3,20-dione-16,17-acetonide-21,21-bis-n-butyl ether,
9α-chloro-6α-fluoro-11β,16α,17α,21,21-pentahydroxypregna-1,5-diene-3,20-dione-16,17-acetonide-21,21-bis-n-butyl ether,
6α,9α-difluoro-11β,17α,21,21-tetrahydroxy-16α-methylpregna-1,5-diene-3,20-dione-21,21-bis-n-butyl ether, 6α,9α-difluoro-11β,17α,21,21-tetrahydroxy-16α-methylpregna-1,5-diene-3,20-dione-17-caprylate-21,21-bis-n-butyl ether, 6α,9α-difluoro-11β,17α,21,21-tetrahydroxy-16α-methylpregna-1,5-diene-3,20-dione-17-benzoate-21,21-bis-n-butyl ether, 9α-fluoro-11β,17α,21,21-tetrahydroxy-16β-methyl-pregna-5-ene-3,20-dione-21,21-bis-n-butyl ether, 6α,9α-difluoro-11β,17α,21,21-tetrahydroxy-16α-methylpregna-1,5-diene-3,20-dione-17-acetate-21,21-bis-n-butyl ether, 11β,16α,17α,21,21-pentahydroxypregn-5-ene-3,20-dione-16,17-acetonide-21,21-bis-n-butyl ether, and 6α-chloro-11β,16α,17α,21,21-pentahydroxypregn-5-ene-3,20-dione-16,17-acetonide-21,21-bis-n-butyl ether.

What is claimed is:

1. A compound having the formula:

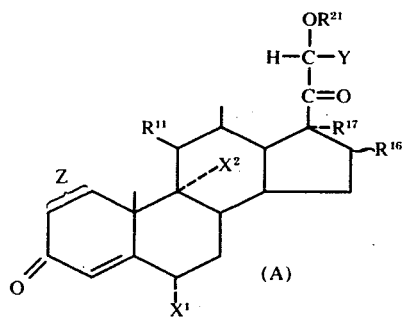

wherein:
R¹¹ is chloro or hydroxy;
R¹⁶ independently is methyl;
R¹⁷ independently is hydroxy or acyloxy having 2 to 8 carbon atoms or R¹⁶ and R¹⁷ taken together are 16α,17α-isopropylidenedioxy;
R²¹ is lower alkyl having 1 to 8 carbon atoms;
X¹ and X² are independently hydrogen, chloro or fluoro, with the proviso that when R¹¹ is chloro, X² is chloro;
Y is OR²¹, Sr²¹', bromo, chloro, cyano, thiocyano or azido in which R²¹' is lower alkyl having 1 to 8 carbon atoms or phenyl and R²¹ is as defined above but independent thereof with the proviso that when Y is OR²¹, R¹⁶ and R¹⁷ are 16α,17α-isopropylidenedioxy; and
Z is a single or double bond.

2. A compound having the formula

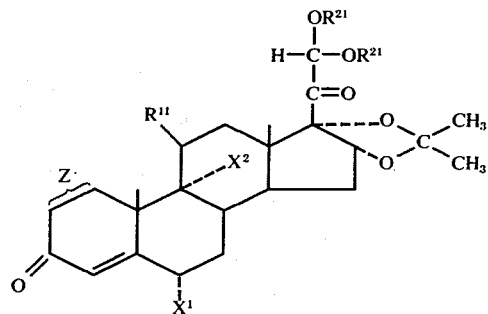

wherein:
R¹¹ is chloro or hydroxy;

both R²¹ groups are identical lower alkyls having 1 to 8 carbon atoms;
X¹ and X² are independently hydrogen, chloro or fluoro with the proviso that when R¹¹ is chloro, X² is chloro; and Z is a single or double bond.

3. The compound of claim 2 which is 6α,9α-difluoro-11β,16α,17α,21,21-pentahydroxypregna-1,4-diene-3,20-dione-16,17-acetonide-21,21-bis-methyl ether.

4. The compound of claim 2 which is 6α-fluoro-11β,16α,17α,21,21-pentahydroxypregna-1,4-diene-3,20-dione-16,17-acetonide-21,21-bis-methyl ether.

5. The compound of claim 2 which is 6α,9α-difluoro-11β,16α,17α,21,21-pentahydroxypregn-4-ene-3,20-dione-16,17-acetonide-21,21-bis-methyl ether.

6. The compound of claim 2 which is 6α-fluoro-11β,16α,17α,21,21-pentahydroxypregn-4-ene-3,20-dione-16,17-acetonide-21,21-bis-methyl ether.

7. The compound of claim 2 which is 9α,11β-dichloro-6α-fluoro-16α,17α,21,21-tetrahydroxypregna-1,4-diene-3,20-dione-16,17-acetonide-21,21-bis-methyl ether.

8. The compound of claim 2 which is 9α-fluoro-11β,16α,17α,21,21-pentahydroxypregna-1,4-diene-3,20-dione-16,17-acetonide-21,21-bis-methyl ether.

9. The compound of claim 2 which is 11β,16α,17α,21,21-pentahydroxypregn-4-ene-3,20-dione-16,17-acetonide-21,21-bis-methyl ether.

10. The compound of claim 2 which is 11β,16α,17α,21,21-pentahydroxypregna-1,4-diene-3,20-dione-16,17-acetonide-21,21-bis-methyl ether.

11. The compound of claim 2 which is 6α-chloro-11β,16α,17α,21,21-pentahydroxypregn-4-ene-3,20-dione-16,17-acetonide-21,21-bis methyl ether.

12. The compound of claim 2 which is 6α,9α-difluoro-11β,16α,17α,21,21-pentahydroxypregna-1,4-diene-3,20-dione-16,17-acetonide-21,21-bis-ethyl ether.

13. The compound of claim 2 which is 60α,9α-difluoro-11β,16α,17α,21,21-pentahydroxypregna-1,4-diene-3,20-dione-16,17-acetonide-21,21-bis-n-propyl ether.

14. The compound of claim 1 which is 21-azido-6α,9α-difluoro-11β,16α,17α,21-tetrahydroxypregna-1,4-diene-3,20-dione-16,17-acetonide-21-methyl ether.

15. The compound of claim 1 which is 6α,9α-difluoro-11β,16α,17α,21-tetrahydroxy-21-thiocyano-pregna-1,4-diene-3,20-dione-16,17-acetonide-21-methyl ether.

16. The compound of claim 1 which is 21-cyano-6α,9α-difluoro-11β,16α,17α,21-tetrahydroxypregna-1,4-diene-3,20-dione-16,17-acetonide-21-methyl ether.

17. The compound of claim 1 which is 6α,9α-difluoro-11β,16α,17α,21-tetrahydroxy-21-thiophenyl-pregna-1,4-diene-3,20-dione-16,17-acetonide-21-methyl ether.

18. The compound of claim 1 which is 6α,9α-difluoro-11β,16α,17α,21-tetrahydroxy-21-thioethyl-pregna-1,4-diene-3,20-dione-16,17-acetonide-21-methyl ether.

19. The compound of claim 1 which is 21-chloro-6α,9α-difluoro-11β,16α,17α,21-tetrahydroxypregna-1,4-diene-3,20-dione-16,17-acetonide-21-methyl ether.

20. A compound selected from the group represented by the following formulas:

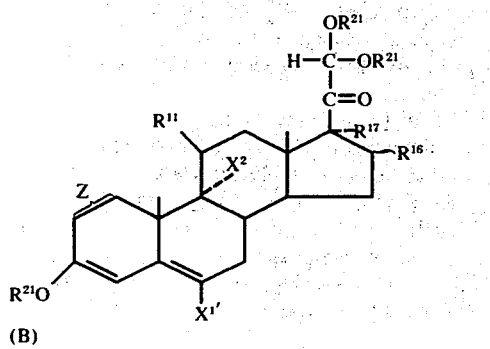

(B)

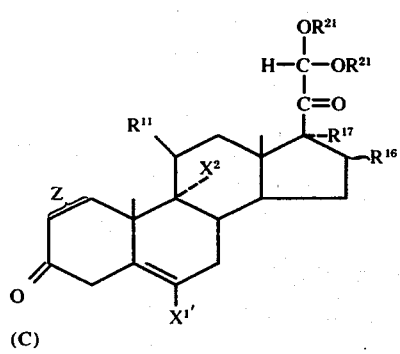

(C)

wherein:
$R^{11}$ is chloro or hydroxy;
$R^{16}$ independently is methyl;
$R^{17}$ independently is hydroxy or acyloxy having 2 to 8 carbon atoms or $R^{16}$ and $R^{17}$ taken together are 16α,17α-isopropylidenedioxy;
all $R^{21}$'s are the same lower alkyl having 1 to 8 carbon atoms;
Z is a single or double bond;
$X^{1'}$ is hydrogen, chloro of fluoro when Z is a single bond and chloro or fluoro when Z is a double bond, and
$X^{2}$ is hydrogen, fluoro or chloro, with the proviso that when $R^{11}$ is chloro, $X^{2}$ is chloro.

21. A compound of claim 20 having Formula (B).
22. A compound of claim 20 having Formula (C).
23. A pharmaceutical composition useful for treating inflammatory disorders comprising a pharmaceutically acceptable non-toxic carrier in admixture with an effective amount of a compound having the formula:

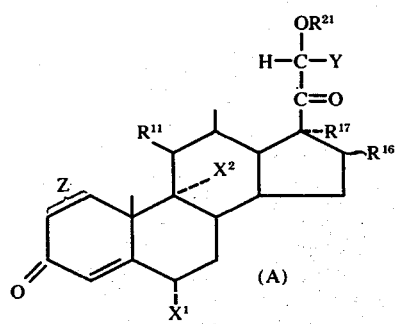

(A)

wherein:
$R^{11}$ is chloro or hydroxy;
$R^{16}$ independently is methyl;
$R^{17}$ independently is hydroxy or acyloxy having 2 to 8 carbon atoms or $R^{16}$ and $R^{17}$ taken together are 16α,17α-isopropylidenedioxy;
$R^{21}$ is lower alkyl having 1 to 8 carbon atoms;
$X^{1}$ and $X^{2}$ are independently hydrogen, chloro or fluoro, with the proviso that when $R^{11}$ is chloro, $X^{2}$ is chloro;
Y is $OR^{21}$, $SR^{21'}$, bromo, chloro, cyano, thiocyano or azido in which $R^{21'}$ is lower alkyl having 1 to 8 carbon atoms or phenyl and $R^{21}$ is as defined above but independent thereof with the proviso that when Y is $OR^{21}$, $R^{16}$ and $R^{17}$ are 16α,17α-isopropylidenedioxy; and
Z is a single or double bond.

24. A pharmaceutical composition useful for treating inflammatory disorders comprising a pharmaceutically acceptable non-toxic carrier in admixture with an effective amount of a compound selected from the group represented by the formulas:

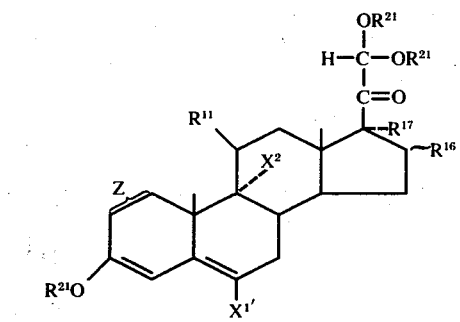

(B)

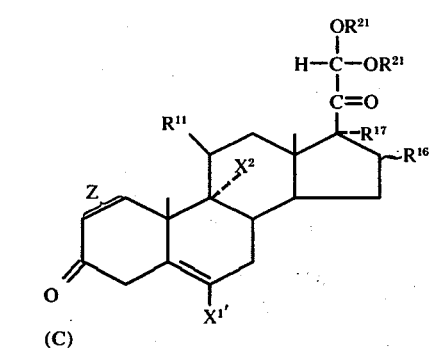

(C)

wherein:
$R^{11}$ is chloro or hydroxy;
$R^{16}$ independently is methyl;
$R^{17}$ independently is hydroxy or acyloxy having 2 to 8 carbon atoms or $R^{16}$ and $R^{17}$ taken together are 16α,17α-isopropylidenedioxy;
all $R^{21}$'s are the same lowr alkyl having 1 to 8 carbon atoms;
Z is a single or double bond;
$X^{1'}$ is hydrogen, chloro or fluoro when Z is a single bond and chloro or fluoro when Z is a double bond; and
$X^{2}$ is hydrogen fluoro or chloro, with the proviso that when $R^{11}$ is chloro, $X^{2}$ is chloro.

25. A method for relieving symptoms associated with inflammatory disorders comprising administering an effective amount of a compound having the formula:

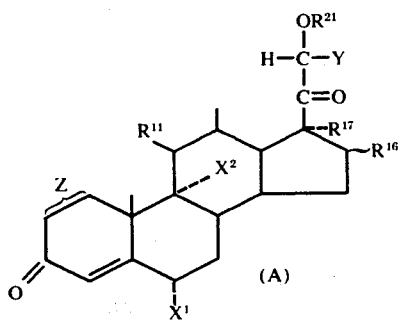

(A)

wherein:
$R^{11}$ is chloro or hydroxy;
$R^{16}$ independently is methyl;
$R^{17}$ independently is hydroxy or acyloxy having 2 to 8 carbon atoms or $R^{16}$ and $R^{17}$ taken together are $16\alpha,17\alpha$-isopropylidenedioxy;
$R^{21}$ is lower alkyl having 1 to 8 carbon atoms;
$X^1$ and $X^2$ are independently hydrogen, chloro or fluoro, with the proviso that when $R^{11}$ is chloro, $X^2$ is chloro;
Y is $OR^{21}$, $SR^{21'}$, bromo, chloro, cyano, thiocyano or azido in which $R^{21'}$ is lower alkyl having 1 to 8 carbon atoms or phenyl and $R^{21}$ is as defined above but independent thereof with the proviso that when Y is $OR^{21}$, $R^{16}$ and $R^{17}$ are $16\alpha,17\alpha$-isopropylidenedioxy; and
Z is a single or double bond; or a pharmaceutical composition containing same.

26. A method for relieving symptoms associated with inflammatory disorders comprising administering an effective amount of a compound selected from the group represented by the formulas:

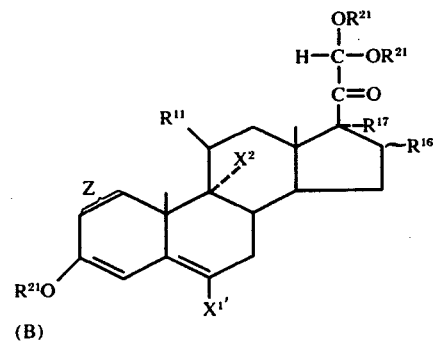

(B)

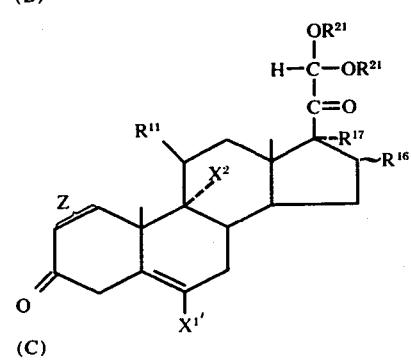

(C)

wherein:
$R^{11}$ is chloro or hydroxy;
$R^{16}$ independently is methyl;

$R^{17}$ independently is hydroxy or acyloxy having 2 to 8 carbon atoms or $R^{16}$ and $R^{17}$ taken together are $16\alpha,17\alpha$-isopropylidenedioxy;
all $R^{21}$'s are the same lower alkyl having 1 to 8 carbon atoms;
Z is a single or double bond;
$X^{1'}$ is hydrogen, chloro or fluoro when Z is a single bond and chloro or fluoro when Z is a double bond
$X^2$ is hydrogen, chloro or fluoro, with the proviso that when $R^{11}$ is chloro, $X^2$ is chloro; or a pharmaceutical composition containing same.

27. A process for preparing a compound selected from the group represented by the formulas:

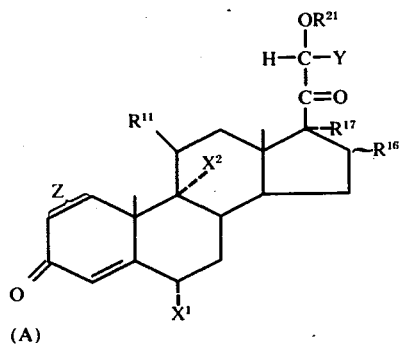

(A)

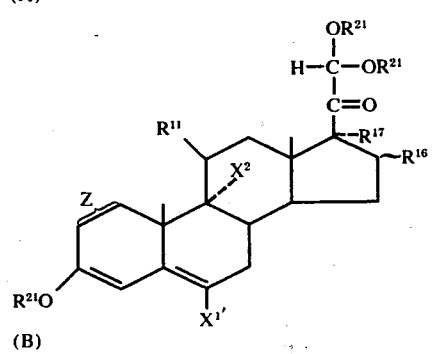

(B)

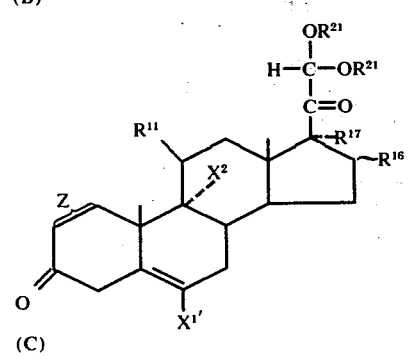

(C)

wherein:
$R^{11}$ is chloro or hydroxy;
$R^{16}$ independently is methyl;
$R^{17}$ independently is hydroxy or acyloxy having 2 to 8 carbon atoms or $R^{16}$ and $R^{17}$ taken together are $16\alpha,17\alpha$-isopropylidenedioxy;
$R^{21}$ is lower alkyl having 1 to 8 carbon atoms and all $R^{21}$'s are the same lower alkyl in compounds of Formulas (B) and (C);
Z is a single or double bond;
Y is $OR^{21}$, $SR^{21'}$, bromo, chloro, cyano, thiocyano or azido in which $R^{21'}$ is lower alkyl having 1 to 8 carbon atoms or phenyl and $R^{21}$ is as defined above, but independent thereof;

$X^{1'}$ and $X^2$ are independently hydrogen, chloro or fluoro, with the proviso that when $R^{11}$ is chloro, $X^2$ is chloro; and $X^{1'}$ is hydrogen, chloro or fluoro when Z is a single bond and chloro or fluoro when Z is a double bond;

which process comprises:
1. for the preparation of compounds of Formula (A) wherein Y is halo, treating a 21-aldehyde hemiacetal with a halogenating agent to obtain a 21-halo-21-alkyl ether;
2. for the preparation of compounds of Formula (A) wherein Y is $OR^{21}$, $SR^{21'}$, cyano, thiocyano or azido, treating a 21-halo-21-alkyl ether with a compound of the formula

MY wherein M is an alkali metal and Y is $OR^{21}$, $SR^{21'}$, cyano, thiocyano or azido to obtain the corresponding compound of Formula (A);
3. for the preparation of compounds of Formula (A) wherein Z is a double bond, $X^1$ is hydrogen and Y is $OR^{21}$, treating a 21-aldehyde hydrate wherein Z is a double bond and $X^1$ is hydrogen with a trialkyl orthoformate in the presence of a strong acid to obtain a 21,21-bis alkyl ether of Formula (A);
4. for the preparation of compounds of (B), treating a 21-aldehyde hydrate wherein $X^{1'}$ is chloro or fluoro when Z is a double bond and hydrogen, chloro or fluoro when Z is a single bond, with a trialkyl orthoformate in the presence of a strong acid to obtain a 3-alkoxy-3,5-dien-21-acetal of Formula (B);
5. for the preparation of compounds of Formula (C), treating a 3-alkoxy-3,5-dien-21-acetal of Formula (B) with an inorganic acid to obtain a 3-oxo-5-en-21-acetal of Formula (C);
6. for the preparation of compounds of Formula (A) wherein $X^1$ is hydrogen, chloro or fluoro when Z is a single bond and chloro or fluoro when Z is a double bond and Y is $OR^{21}$, treating a 3-oxo-5-en-21-acetal of Formula (C) with a base to obtain the 21,21-bis alkyl ether of Formula (A); and/or
7. for the preparation of compounds of Formula (A) wherein $X^1$ is hydrogen, chloro or fluoro when Z is a single bond and chloro or fluoro when Z is a double bond and Y is $OR^{21}$, treating a compound of Formula (B) with a strong acid to obtain a 21,21-bis alkyl ether of Formula (A).

28. A pharmaceutical composition useful for treating inflammatory disorders comprising a pharmaceutically acceptable non-toxic carrier in admixture with an effective amount of a compound having the formula

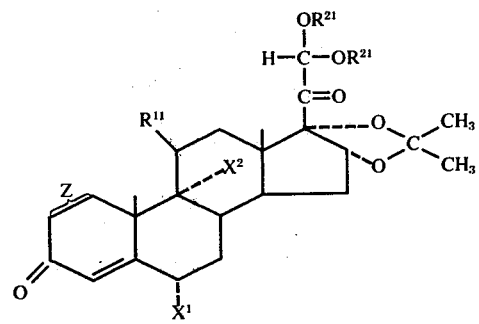

wherein:
$R^{11}$ is chloro or hydroxy;
both $R^{21}$ groups are identical lower alkyls containing 1 to 8 carbon atoms;
$X^1$ and $X^2$ are independently hydrogen, chloro or fluoro with the proviso that when $R^{11}$ is chloro, $X^2$ is chloro; and
Z is a single or double bond.

29. A method for relieving symptoms associated with inflammatory disorders comprising administering an effective amount of a compound having the formula

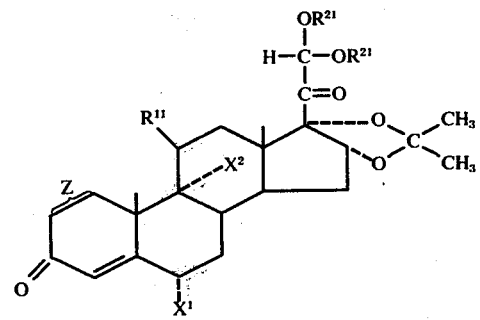

wherein:
$R^{11}$ is chloro or hydroxy;
both $R^{21}$ groups are identical lower alkyls containing 1 to 8 carbon atoms;
$X^1$ and $X^2$ are independently hydrogen, chloro or fluoro with the proviso that when $R^{11}$ is chloro, $X^2$ is chloro; and
Z is a single or double bond; or a pharmaceutical composition containing same.

* * * * *

UNITED STATES PATENT AND TRADEMARK OFFICE
CERTIFICATE OF CORRECTION

PATENT NO. : 4,011,315
DATED : March 8, 1977
INVENTOR(S) : MICHAEL MARX ET AL

It is certified that error appears in the above-identified patent and that said Letters Patent are hereby corrected as shown below:

Column 1, the first formula drawing

"
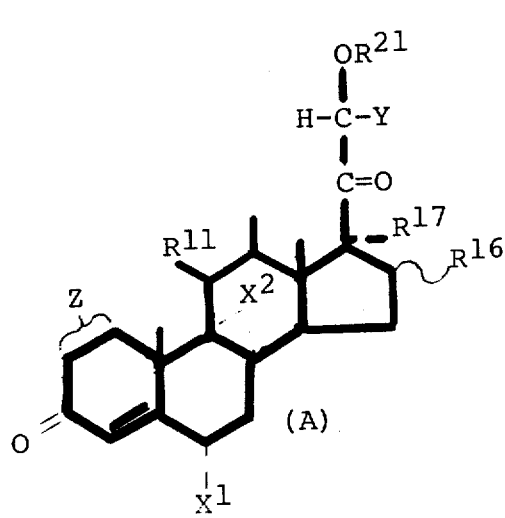
"

should read --

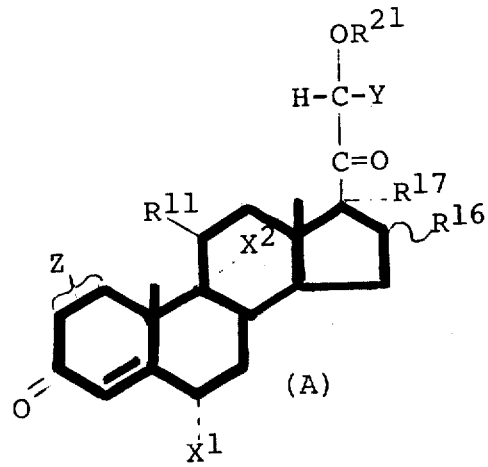

--.

UNITED STATES PATENT AND TRADEMARK OFFICE
CERTIFICATE OF CORRECTION

PATENT NO. : 4,011,315
DATED : March 8, 1977
INVENTOR(S) : MICHAEL MARX ET AL

It is certified that error appears in the above-identified patent and that said Letters Patent are hereby corrected as shown below:

Column 3, line 7 "glycol or the" should read -- glycol monostearate, or the --. Column 4, line 14 "carpyrlate," should read -- caprylate, --. Column 4, the top right formula drawing

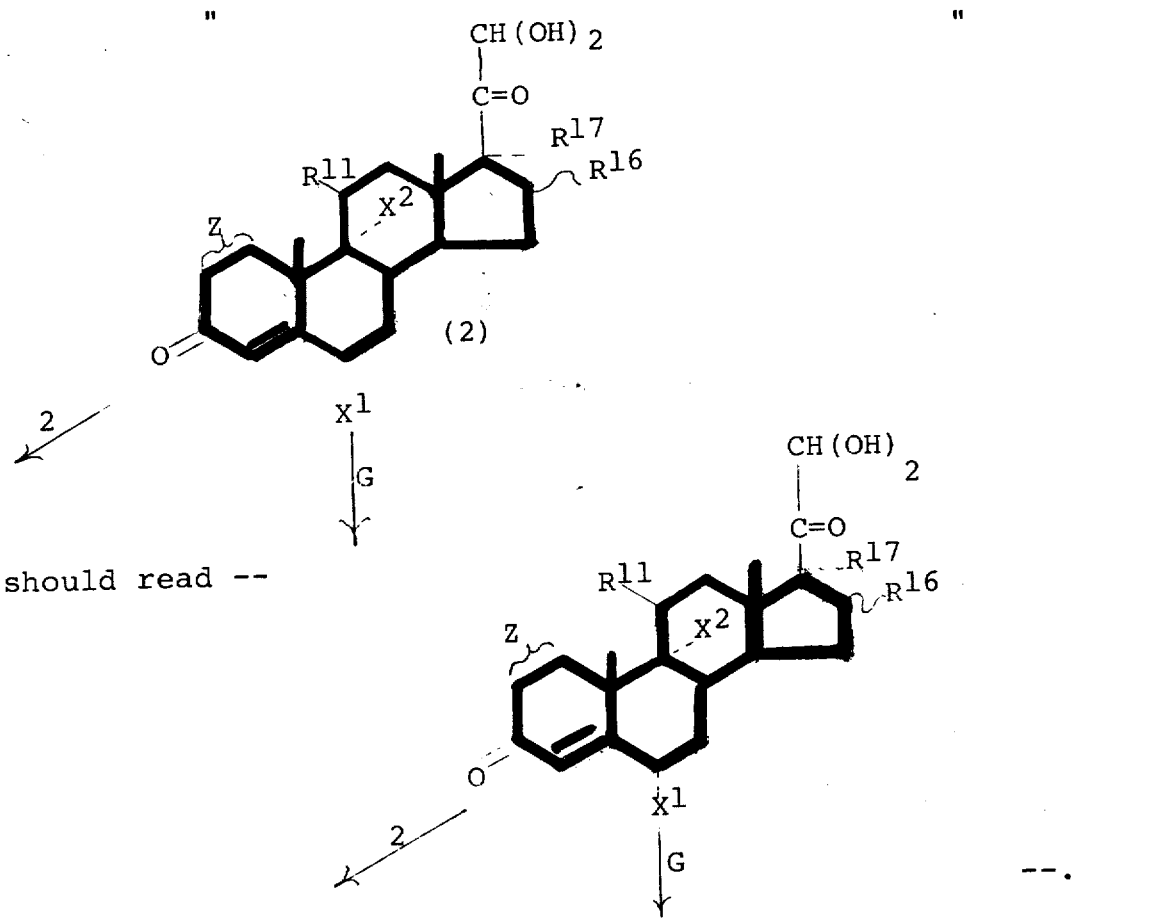

UNITED STATES PATENT AND TRADEMARK OFFICE
CERTIFICATE OF CORRECTION

PATENT NO. : 4,011,315

DATED : March 8, 1977

INVENTOR(S) : MICHAEL MARX ET AL

It is certified that error appears in the above-identified patent and that said Letters Patent are hereby corrected as shown below:

Column 5, line 41 "50° to 30°" should read -- 5 to 30° --. Column 5, line 44 "100°C. for" should read -- 100 to 130°C. for --. Column 5, line 48 "heniacetal" should read -- hemiacetal --. Column 6, line 36 "peferably" should read -- preferably --. Column 6, line 47 "Y=λ" should read -- Y-cyano), --. Column 6, line 49 "21thioalkyl" should read -- 21-thioalkyl --. Column 6, line 49 "Y=λ" should read -- Y=thioalkyl --. Column 7, line 34, "(C) and be" should read -- (C) can be --. Column 7, line 34, "for U.S. Pat." should read -- for example from U.S. Pat. --. Column 7, lines 58 and 59 "1-7α," should read -- 17α, --. Column 8, line 22 "1,4-3,20,21-trione-" should read -- 1,4-diene-3,20,21-trione- --. Column 8, line 49 "21-butyl" should read -- 21-sec-butyl --. Column 10, lines 21 and 22 "1-7α" should read -- 17α --. Column 10, line 57 "empimer" should read -- epimer --. Column 15, line 39 "21tetrahydroxy" should read -- 21-tetrahydroxy--. Column 16, line 29 "paragraph (a)" should read -- paragraph a) --. Column 22, line 25 "17acetate-" should read -- 17-acetate- --. Column 22, line 36 "-21-n-propyl" should read -- -21-methyl-21-n-propyl --. Column 22, line 39 "6Oα,9α-difluoro" should read -- 6α,9α-difluoro --. Column 23, line 15 "21n-propyl" should read -- 21-n-propyl --. Column 23, line 20 "acetonide-21-n-propyl" should read -- acetonide-21-ethyl-21-n-propyl --. Column 23, line 28 "16αmethylpregna" should read -- 16α-methyl-pregna --. Column 23, line 36 "ethyl21n-propyl" should read -- ethyl-21-n-propyl --. Column 23, line 39 "21n-propyl" should read -- 21-n-propyl --. Column 23, line 41 "21n-propyl" should read -- 21-n-propyl --. Column 23, line 58 "21n-butyl" should read -- 21-n-butyl --. Column 24, line 3 "21 n-octyl" should read -- 21-n-octyl --. Column 24, line 10 "11β,16;6O,17α" should read -- 11β,16α,17α --. Column 24, line 27 "17;6O,21,21-" should read -- 17α,21,21- --. Column 24, line 31 "17acetate" should read -- 17-acetate --. Column 24, line 42 "21n-hexyl" should read --21-n-hexyl --.

UNITED STATES PATENT AND TRADEMARK OFFICE
CERTIFICATE OF CORRECTION

PATENT NO. : 4,011,315

DATED : March 8, 1977

INVENTOR(S) : MICHAEL MARX ET AL

It is certified that error appears in the above–identified patent and that said Letters Patent are hereby corrected as shown below:

Column 24, line 50 "hexyl-n-octyl" should read -- hexyl-21-n-octyl --. Column 24, line 53 "21n-amyl" should read -- 21-n-amyl --. Column 24, line 63 "21-azipo" should read -- 21-azido --. Column 25, line 2 "methylpregna 1,4-diene" should read -- methylpregna-1,4-diene --. Column 25, line 14 "4ene" should read -- 4-ene --. Column 25, line 33 "11β,16α;60,17α" should read -- 11β,16α,17α, --. Column 26, line 56 "thoicyano" should read -- thiocyano --. Column 26, lines 64 and 65 "1643,5-dien--" should read -- 21-thiocyano-pregn-4-ene-3,20-dione-21- --. Column 27, line 10 "chloro-6α;1" should read -- chloro-6α --. Column 27, line 29 "3,20-16," should read -- 3,20-dione-16, --. Column 27, line 50 "21n-propyl" should read -- 21-n-propyl --. Column 27, line 54 "fluoro-11α" should read -- fluoro-11β --. Column 28, line 16 "cyano6α,9α" should read -- cyano-6α,9α --. Column 28, line 25 "cyano9α" should read -- cyano-9α --. Column 28, line 41 "16,60,17α,21" should read -- 16α,17α,21 --. Column 31, lines 30 and 31 "3,20-dione-17-caprylate-21-methyl" should read -- 3,20-dione-21-methyl --. Column 32, line 68 "17-aceotnide" should read -- 17-acetonide --. Column 35, line 20 "3,5-dien-dien-20" should read -- 3,5-dien-20 --. Column 35, lines 48 and 49 "hexahydroxyprenga" should read -- hexahydroxy-pregna --. Column 36, line 21 "60α-fluoro" should read -- 6α-fluoro --. Column 36, line 27 "60α6α-fluoro" should read --6α-fluoro --. Column 36, line 40 "mthylpregna" should read -- methylpregna --.

UNITED STATES PATENT AND TRADEMARK OFFICE
CERTIFICATE OF CORRECTION

PATENT NO. : 4,011,315
DATED : March 8, 1977
INVENTOR(S) : MICHAEL MARX ET AL

It is certified that error appears in the above-identified patent and that said Letters Patent are hereby corrected as shown below:

Claim 1, column 39 the first formula drawing

"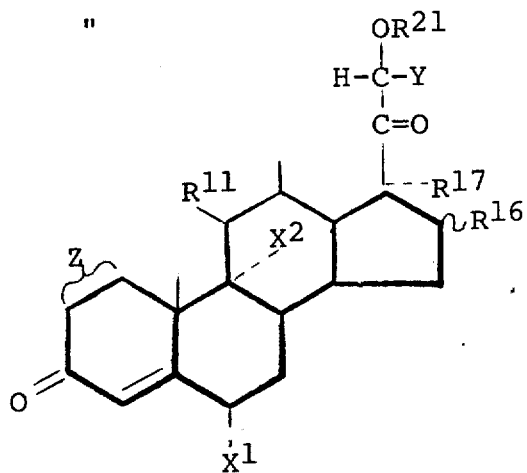"

should read --

"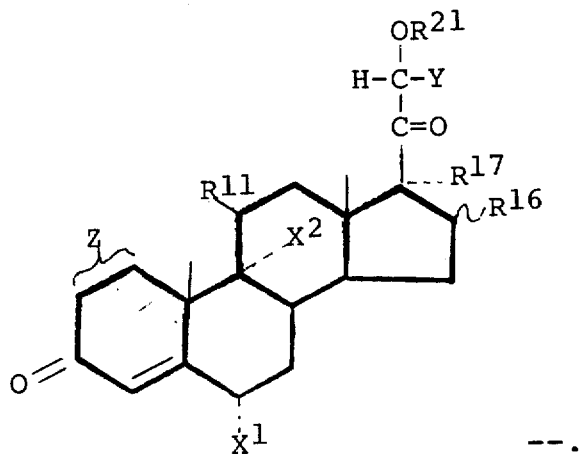" --.

Claim 1, line 12, column 39, line 45 "Sr$^{21'}$" should read -- SR$^{21'}$ --. Claim 9, lines 1 and 2, column 40, lines 27 and 28 "1-7α" should read -- 17α --. Claim 10, lines 1 and 2, column 40, lines 30 and 31 "1-7α," should read -- 17α, --. Claim 13, line 1, column 40, line 40 "60α,9α-" should read -- 6α,9α- --.

UNITED STATES PATENT AND TRADEMARK OFFICE
CERTIFICATE OF CORRECTION

PATENT NO. : 4,011,315
DATED : March 8, 1977
INVENTOR(S) : MICHAEL MARX ET AL

It is certified that error appears in the above-identified patent and that said Letters Patent are hereby corrected as shown below:

Claim 25, column 43 the first formula drawing

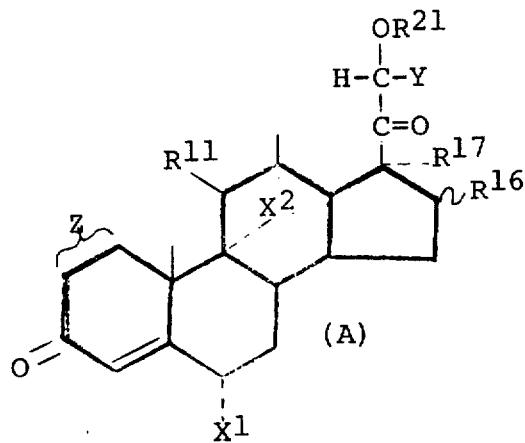

should read --

Signed and Sealed this

Third Day of January 1978

[SEAL]

Attest:

RUTH C. MASON
Attesting Officer

LUTRELLE F. PARKER
Acting Commissioner of Patents and Trademarks